(12) United States Patent
Ohshima et al.

(10) Patent No.: US 8,192,736 B2
(45) Date of Patent: Jun. 5, 2012

(54) REMEDY FOR ENDOMETRIOSIS

(75) Inventors: Etsuo Ohshima, Shizuoka (JP);
Hirokazu Kawasaki, Shizuoka (JP);
Naoya Kimoto, Shizuoka (JP); Akihiko Watanabe, Shizuoka (JP)

(73) Assignee: Kyowa Hakko Kirin Co., Ltd, Tokyo (JP)

( * ) Notice: Subject to any disclaimer, the term of this patent is extended or adjusted under 35 U.S.C. 154(b) by 414 days.

(21) Appl. No.: 11/666,695

(22) PCT Filed: Oct. 28, 2005

(86) PCT No.: PCT/JP2005/019871
§ 371 (c)(1),
(2), (4) Date: Jun. 29, 2007

(87) PCT Pub. No.: WO2006/046689
PCT Pub. Date: May 4, 2006

(65) Prior Publication Data
US 2009/0252723 A1 Oct. 8, 2009

(30) Foreign Application Priority Data

Oct. 28, 2004 (JP) ................................. 2004-314031
Jun. 9, 2005 (JP) ................................. 2005-169027

(51) Int. Cl.
A61K 38/00 (2006.01)
A61K 39/395 (2006.01)
C07K 16/24 (2006.01)
C07K 16/28 (2006.01)
C07K 14/54 (2006.01)
C07K 14/715 (2006.01)

(52) U.S. Cl. ............... 424/130.1; 424/143.1; 424/145.1; 424/158.1; 514/1; 514/1.1; 530/350; 530/351; 530/387.1; 530/388.1; 530/388.22; 530/388.23; 530/389.1; 530/389.2

(58) Field of Classification Search .......................... None
See application file for complete search history.

(56) References Cited

U.S. PATENT DOCUMENTS

| 5,783,184 A | * | 7/1998 | Appelbaum et al. ....... 424/130.1 |
| 5,916,767 A | * | 6/1999 | Takatsu et al. ............... 435/69.1 |
| 6,018,032 A | | 1/2000 | Koike et al. |
| 6,129,913 A | | 10/2000 | Ames et al. |
| 6,540,980 B1 | * | 4/2003 | Blumenthal et al. ......... 424/9.34 |

FOREIGN PATENT DOCUMENTS

| EP | 1 266 663 A1 | 12/2002 |
| JP | 2002-187855 A | 7/2002 |
| WO | 97-10354 A1 | 3/1997 |
| WO | 2000-59547 A2 | 10/2000 |
| WO | 2001-60405 A1 | 8/2001 |
| WO | 2003-085089 A2 | 10/2003 |

OTHER PUBLICATIONS

Sferruzzi-Perri et al. Interleukin-5 transgene expression and eosinophilia are associated with retarded mammary gland development in mice. Biol Reproduct 69: 224-233, 2003.*
Robertson et al. Uterine eosinophils and reproductive performance in interleukin 5-deficient mice. J Reprod Fertil 120: 423-432, 2000.*
Tomaki et al. Eosinophilopoiesis in a murine model of allergic airway eosinophilia: involvement of bone marrow IL-5 and IL-5 receptor alpha. J Immunol 165:4040-4050, 2000.*
Devos et al. Interluekin-5 and its receptor: a drug target for eosinophilia associated with chronic allergic disease. J Leukoc Biol 57: 813-819, 1995.*
Garlisi et al. IL-5 inhibition as a therapy for allergic disease. Pulmon Pharmacol Therap 12: 81-85, 1999.*
Lalani et al. Biology of IL-5 in health and disease. Ann Allergy Asthma Immunol 82: 317-333, 1999.*
Blumenthal et al. Unique molecular markers in human endometriosis: implications for diagnosis and therapy. Reprod Med Rev 11(2): 105-119, 2003.*
Min et al. Sophopricoside analogs as the IL-5 inhibitors from Sophora japonica. Planta Medica 65: 408-412, 1999.*
Morokata et al. Effect of a novel interleukin-5 receptor antagonist, YM-90709, on antigen-induced eosinophil infiltration into the airway of BDF1 mice. Immunol Letters 98: 161-165, 2005.*
Rosas et al. Functional analysis of the interleukin-5 receptor antagonist peptide, AF18748. Cytokine 26: 247-254, 2004.*
Uings et al. Development of IL-5 receptor antagonists. Curr Pharmaceuti Design 8: 1837-1844, 2002.*
England et al. A potent dimeric peptide antagonist of interleukin-5 that binds two interleukin-5 receptor alpha chains. Proc Natl Acad Sci USA 97(12): 6862-6867, 2000.*
Extended European Search Report dated Mar. 10, 2008.
N. Koyama et al., "Cytokines in the peritoneal fluid of patients with endometriosis", Int. J. Gynecol. Obstet., 1993, pp. 45-50, vol. 43, International Federation of Gynecology and Obstetrics.
Rosalyn D. Blumenthal, et al.; "Degranulating Eosinophils in Human Endometriosis", American Journal of Pathology, May 2000, vol. 156, No. 5, pp. 1581 to 1588.
Rosalyn D. Blumenthal, et al., "Unique Molecular Markers in Human Endometriosis: Implications for Diagnosis and Therapy"; Expert Reviews in Molecular Medicine, Nov 2001; pp. 1 to 12.
Akira Harada, "Shikyu Naimakusho no EBM to TBM Ensho to Shikyu Naimakusho", Sanfujinka Chiryo, 2003, vol. 86, No. 6, pp. 1048 to 1054.
International Search Report for International Patent Application PCT/JP2005/019871, issued Jan. 17, 2006.
Office Action dated May 31, 2011 from the Japanese Patent Office in counterpart Japanese Application No. 2006-543289, in the name of Kyowa Hakko Kirin Co., Ltd.
Office Action issued on Apr. 6, 2011 by the State Intellectual Property Office of the P.R. of China in the corresponding Chinese Patent Application No. 200580041205.3 in the name of Kyowa Hakko Kirin.
Chinese Office Action issued on Oct. 13, 2011 in counterpart Chinese Application No. 200580041205.3.
Yasumichi Hitoshi et al., "In vivo administration of antibody to murine IL-5 receptor inhibits eosinophilia of IL-5 transgenic mice", International Immunology, 1991, 3(2): 135-139.

* cited by examiner

*Primary Examiner* — Bridget E Bunner
(74) *Attorney, Agent, or Firm* — Sughrue Mion, PLLC

(57) ABSTRACT

The present invention provides a therapeutic agent for endometriosis comprising an interleukin-5 antagonist as an active ingredient.

11 Claims, 2 Drawing Sheets

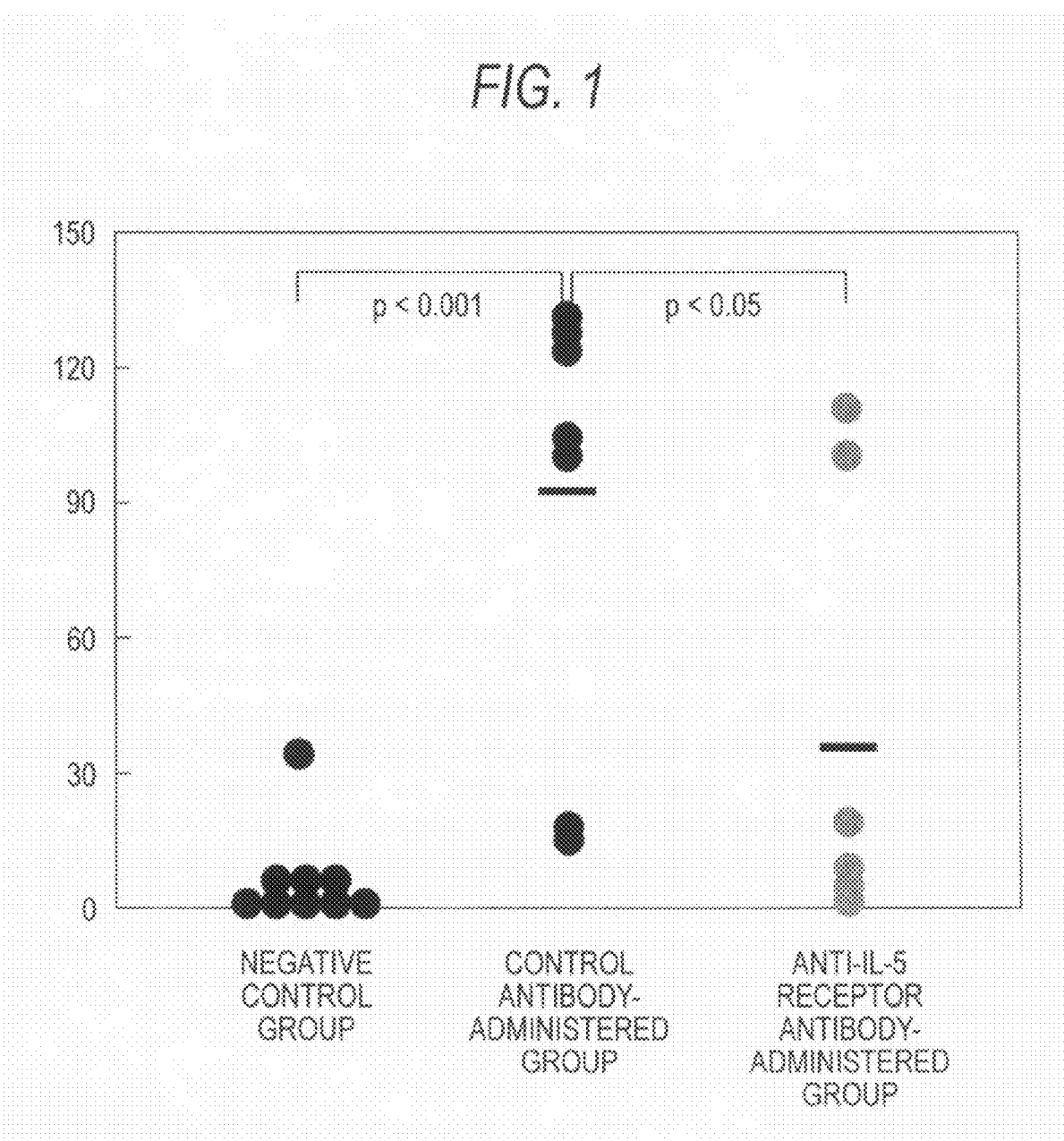

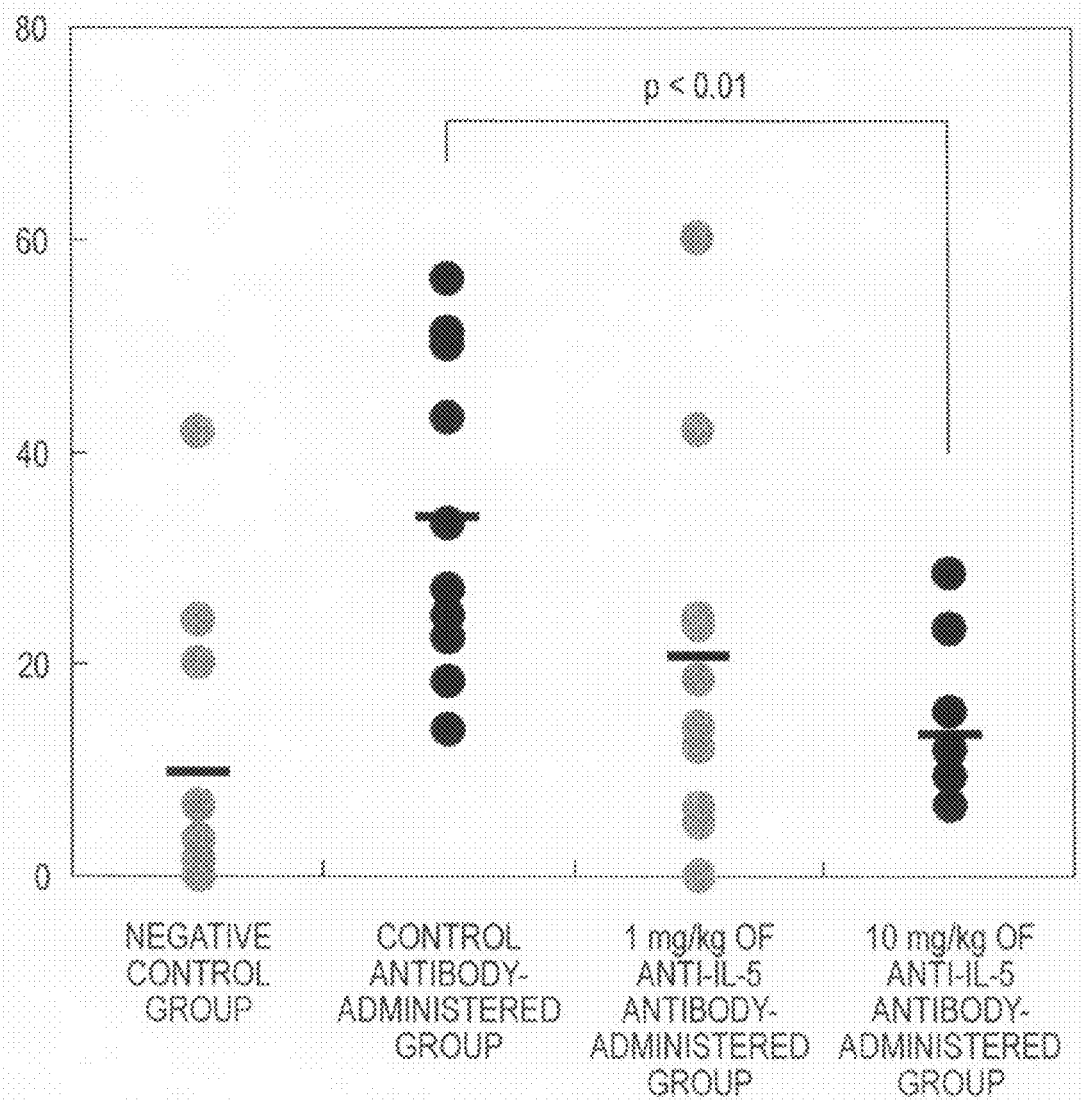

```
                         SEQUENCE LISTING

<160> NUMBER OF SEQ ID NOS: 29

<210> SEQ ID NO 1
<211> LENGTH: 5
<212> TYPE: PRT
<213> ORGANISM: Mus musculus

<400> SEQUENCE: 1

Ser Tyr Val Ile His
 1               5

<210> SEQ ID NO 2
<211> LENGTH: 17
<212> TYPE: PRT
<213> ORGANISM: Mus musculus

<400> SEQUENCE: 2

Tyr Ile Asn Pro Tyr Asn Asp Gly Thr Lys Tyr Asn Glu Arg Phe Lys
 1               5                  10                  15

Gly

<210> SEQ ID NO 3
<211> LENGTH: 12
<212> TYPE: PRT
<213> ORGANISM: Mus musculus

<400> SEQUENCE: 3

Glu Gly Ile Arg Tyr Tyr Gly Leu Leu Gly Asp Tyr
 1               5                  10

<210> SEQ ID NO 4
```

```
<211> LENGTH: 11
<212> TYPE: PRT
<213> ORGANISM: Mus musculus

<400> SEQUENCE: 4

Gly Thr Ser Glu Asp Ile Ile Asn Tyr Leu Asn
 1               5                  10

<210> SEQ ID NO 5
<211> LENGTH: 7
<212> TYPE: PRT
<213> ORGANISM: Mus musculus

<400> SEQUENCE: 5

His Thr Ser Arg Leu Gln Ser
 1               5

<210> SEQ ID NO 6
<211> LENGTH: 9
<212> TYPE: PRT
<213> ORGANISM: Mus musculus

<400> SEQUENCE: 6

Gln Gln Gly Tyr Thr Leu Pro Tyr Thr
 1               5

<210> SEQ ID NO 7
<211> LENGTH: 140
<212> TYPE: PRT
<213> ORGANISM: Mus musculus

<400> SEQUENCE: 7

Met Glu Trp Ser Trp Ile Phe Leu Phe Leu Leu Ser Gly Thr Ala Gly
 1               5                  10                  15

Val His Ser Glu Val Gln Leu Gln Gln Ser Gly Pro Glu Leu Val Lys
             20                  25                  30

Pro Gly Ala Ser Val Lys Met Ser Cys Lys Ala Ser Gly Tyr Thr Phe
         35                  40                  45

Thr Ser Tyr Val Ile His Trp Val Lys Gln Arg Pro Gly Gln Gly Leu
     50                  55                  60

Ala Trp Ile Gly Tyr Ile Asn Pro Tyr Asn Asp Gly Thr Lys Tyr Asn
 65                  70                  75                  80

Glu Arg Phe Lys Gly Lys Ala Thr Leu Thr Ser Asp Arg Ser Ser Ser
                 85                  90                  95

Thr Val Tyr Met Glu Leu Ser Ser Leu Thr Ser Glu Asp Ser Ala Val
            100                 105                 110

Tyr Leu Cys Gly Arg Glu Gly Ile Arg Tyr Tyr Gly Leu Leu Gly Asp
        115                 120                 125

Tyr Trp Gly Gln Gly Thr Thr Leu Thr Val Ser Ser
    130                 135                 140

<210> SEQ ID NO 8
<211> LENGTH: 127
<212> TYPE: PRT
<213> ORGANISM: Mus musculus

<400> SEQUENCE: 8

Met Met Ser Ser Ala Gln Phe Leu Gly Leu Leu Leu Leu Cys Phe Gln
 1               5                  10                  15

Asp Ile Arg Cys Asp Ile Gln Met Thr Gln Ala Thr Ser Ser Leu Ser
             20                  25                  30
```

```
Ala Ser Leu Gly Asp Arg Val Thr Ile Gly Cys Thr Ser Glu Asp
            35                  40                  45

Ile Ile Asn Tyr Leu Asn Trp Tyr Arg Lys Lys Pro Asp Gly Thr Val
 50                  55                  60

Glu Leu Leu Ile Tyr His Thr Ser Arg Leu Gln Ser Gly Val Pro Ser
 65                  70                  75                  80

Arg Phe Ser Gly Ser Gly Ser Gly Thr Asp Tyr Ser Leu Thr Ile Ser
                 85                  90                  95

Asp Leu Glu Gln Glu Asp Ile Ala Thr Tyr Phe Cys Gln Gln Gly Tyr
                100                 105                 110

Thr Leu Pro Tyr Thr Val Gly Gly Thr Lys Leu Glu Ile Lys
            115                 120                 125
```

<210> SEQ ID NO 9
<211> LENGTH: 121
<212> TYPE: PRT
<213> ORGANISM: Artificial Sequence
<220> FEATURE:
<223> OTHER INFORMATION: Synthetic peptide

<400> SEQUENCE: 9

```
Glu Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Val Ile His Trp Val Arg Gln Ala Pro Gly Gln Gly Leu Glu Trp Met
             35                  40                  45

Gly Tyr Ile Asn Pro Tyr Asn Asp Gly Thr Lys Tyr Asn Glu Arg Phe
 50                  55                  60

Lys Gly Arg Val Thr Ile Thr Ala Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Gly Ile Arg Tyr Tyr Gly Leu Leu Gly Asp Tyr Trp Gly
                100                 105                 110

Gln Gly Thr Leu Val Thr Val Ser Ser
            115                 120
```

<210> SEQ ID NO 10
<211> LENGTH: 107
<212> TYPE: PRT
<213> ORGANISM: Artificial Sequence
<220> FEATURE:
<223> OTHER INFORMATION: Synthetic peptide

<400> SEQUENCE: 10

```
Asp Ile Gln Met Thr Gln Ser Pro Ser Ser Leu Ser Ala Ser Val Gly
  1               5                  10                  15

Asp Arg Val Thr Ile Thr Cys Gly Thr Ser Glu Asp Ile Ile Asn Tyr
                 20                  25                  30

Leu Asn Trp Tyr Gln Gln Lys Pro Gly Lys Ala Pro Lys Leu Leu Ile
             35                  40                  45

Tyr His Thr Ser Arg Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Tyr Thr Leu Pro Tyr
                 85                  90                  95
```

```
Thr Phe Gly Gln Gly Thr Lys Val Glu Ile Lys
            100                 105

<210> SEQ ID NO 11
<211> LENGTH: 121
<212> TYPE: PRT
<213> ORGANISM: Artificial Sequence
<220> FEATURE:
<223> OTHER INFORMATION: Synthetic peptide

<400> SEQUENCE: 11

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Val Ile His Trp Val Arg Gln Ala Pro Gly Gln Gly Leu Glu Trp Met
            35                  40                  45

Gly Tyr Ile Asn Pro Tyr Asn Asp Gly Thr Lys Tyr Asn Glu Arg Phe
        50                  55                  60

Lys Gly Arg Val Thr Ile Thr Ala Asp Thr Ser Thr Ser Thr Ala Tyr
 65                  70                  75                  80

Met Glu Leu Ser Ser Leu Arg Ser Glu Asp Thr Ala Val Tyr Leu Cys
                85                  90                  95

Gly Arg Glu Gly Ile Arg Tyr Tyr Gly Leu Leu Gly Asp Tyr Trp Gly
            100                 105                 110

Gln Gly Thr Leu Val Thr Val Ser Ser
        115                 120

<210> SEQ ID NO 12
<211> LENGTH: 121
<212> TYPE: PRT
<213> ORGANISM: Artificial Sequence
<220> FEATURE:
<223> OTHER INFORMATION: Synthetic peptide

<400> SEQUENCE: 12

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Val Ile His Trp Val Arg Gln Ala Pro Gly Gln Gly Leu Ala Trp Met
            35                  40                  45

Gly Tyr Ile Asn Pro Tyr Asn Asp Gly Thr Lys Tyr Asn Glu Arg Phe
        50                  55                  60

Lys Gly Arg Val Thr Ile Thr Ala Asp Arg Ser Thr Ser Thr Ala Tyr
 65                  70                  75                  80

Met Glu Leu Ser Ser Leu Arg Ser Glu Asp Thr Ala Val Tyr Leu Cys
                85                  90                  95

Gly Arg Glu Gly Ile Arg Tyr Tyr Gly Leu Leu Gly Asp Tyr Trp Gly
            100                 105                 110

Gln Gly Thr Leu Val Thr Val Ser Ser
        115                 120

<210> SEQ ID NO 13
<211> LENGTH: 121
<212> TYPE: PRT
<213> ORGANISM: Artificial Sequence
<220> FEATURE:
<223> OTHER INFORMATION: Synthetic peptide

<400> SEQUENCE: 13
```

```
Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Val Ile His Trp Val Arg Gln Arg Pro Gly Gln Gly Leu Ala Trp Met
         35                  40                  45

Gly Tyr Ile Asn Pro Tyr Asn Asp Gly Thr Lys Tyr Asn Glu Arg Phe
     50                  55                  60

Lys Gly Lys Val Thr Ile Thr Ser Asp Arg Ser Thr Ser Thr Val Tyr
 65                  70                  75                  80

Met Glu Leu Ser Ser Leu Arg Ser Glu Asp Thr Ala Val Tyr Leu Cys
                 85                  90                  95

Gly Arg Glu Gly Ile Arg Tyr Tyr Gly Leu Leu Gly Asp Tyr Trp Gly
                100                 105                 110

Gln Gly Thr Leu Val Thr Val Ser Ser
            115                 120

<210> SEQ ID NO 14
<211> LENGTH: 107
<212> TYPE: PRT
<213> ORGANISM: Artificial Sequence
<220> FEATURE:
<223> OTHER INFORMATION: Synthetic peptide

<400> SEQUENCE: 14

Asp Ile Gln Met Thr Gln Ser Pro Ser Ser Leu Ser Ala Ser Val Gly
 1               5                  10                  15

Asp Arg Val Thr Ile Thr Cys Gly Thr Ser Glu Asp Ile Ile Asn Tyr
                20                  25                  30

Leu Asn Trp Tyr Arg Gln Lys Pro Gly Lys Ala Pro Glu Leu Leu Ile
         35                  40                  45

Tyr His Thr Ser Arg Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Tyr Thr Leu Pro Tyr
                 85                  90                  95

Thr Val Gly Gln Gly Thr Lys Val Glu Ile Lys
                100                 105

<210> SEQ ID NO 15
<211> LENGTH: 107
<212> TYPE: PRT
<213> ORGANISM: Artificial Sequence
<220> FEATURE:
<223> OTHER INFORMATION: Synthetic peptide

<400> SEQUENCE: 15

Asp Ile Gln Met Thr Gln Ser Pro Ser Ser Leu Ser Ala Ser Val Gly
 1               5                  10                  15

Asp Arg Val Thr Ile Gly Cys Gly Thr Ser Glu Asp Ile Ile Asn Tyr
                20                  25                  30

Leu Asn Trp Tyr Arg Gln Lys Pro Gly Lys Ala Pro Glu Leu Leu Ile
         35                  40                  45

Tyr His Thr Ser Arg Leu Gln Ser Gly Val Pro Ser Arg Phe Ser Gly
     50                  55                  60

Ser Gly Ser Gly Thr Asp Phe Thr Leu Thr Ile Ser Asp Leu Gln Pro
 65                  70                  75                  80
```

```
Glu Asp Phe Ala Thr Tyr Tyr Cys Gln Gln Gly Tyr Thr Leu Pro Tyr
                85                  90                  95

Thr Val Gly Gln Gly Thr Lys Val Glu Ile Lys
            100                 105

<210> SEQ ID NO 16
<211> LENGTH: 107
<212> TYPE: PRT
<213> ORGANISM: Artificial Sequence
<220> FEATURE:
<223> OTHER INFORMATION: Synthetic peptide

<400> SEQUENCE: 16

Asp Ile Gln Met Thr Gln Ala Thr Ser Ser Leu Ser Ala Ser Val Gly
 1               5                  10                  15

Asp Arg Val Thr Ile Gly Cys Gly Thr Ser Glu Asp Ile Ile Asn Tyr
            20                  25                  30

Leu Asn Trp Tyr Arg Lys Lys Pro Gly Lys Ala Pro Glu Leu Leu Ile
        35                  40                  45

Tyr His Thr Ser Arg Leu Gln Ser Gly Val Pro Ser Arg Phe Ser Gly
 50                  55                  60

Ser Gly Ser Gly Thr Asp Phe Thr Leu Thr Ile Ser Asp Leu Gln Pro
65                  70                  75                  80

Glu Asp Phe Ala Thr Tyr Phe Cys Gln Gln Gly Tyr Thr Leu Pro Tyr
                85                  90                  95

Thr Val Gly Gln Gly Thr Lys Val Glu Ile Lys
            100                 105

<210> SEQ ID NO 17
<211> LENGTH: 107
<212> TYPE: PRT
<213> ORGANISM: Artificial Sequence
<220> FEATURE:
<223> OTHER INFORMATION: Synthetic peptide

<400> SEQUENCE: 17

Asp Ile Gln Met Thr Gln Ala Thr Ser Ser Leu Ser Ala Ser Val Gly
 1               5                  10                  15

Asp Arg Val Thr Ile Gly Cys Gly Thr Ser Glu Asp Ile Ile Asn Tyr
            20                  25                  30

Leu Asn Trp Tyr Arg Lys Lys Pro Gly Lys Ala Val Glu Leu Leu Ile
        35                  40                  45

Tyr His Thr Ser Arg Leu Gln Ser Gly Val Pro Ser Arg Phe Ser Gly
 50                  55                  60

Ser Gly Ser Gly Thr Asp Tyr Thr Leu Thr Ile Ser Asp Leu Gln Pro
65                  70                  75                  80

Glu Asp Phe Ala Thr Tyr Phe Cys Gln Gln Gly Tyr Thr Leu Pro Tyr
                85                  90                  95

Thr Val Gly Gln Gly Thr Lys Val Glu Ile Lys
            100                 105

<210> SEQ ID NO 18
<211> LENGTH: 5
<212> TYPE: PRT
<213> ORGANISM: Mus musculus

<400> SEQUENCE: 18

Asp Thr Tyr Met His
 1               5
```

```
<210> SEQ ID NO 19
<211> LENGTH: 17
<212> TYPE: PRT
<213> ORGANISM: Mus musculus

<400> SEQUENCE: 19

Arg Ile Asp Pro Ala Asn Gly Asn Thr Lys Ser Asp Pro Lys Phe Gln
 1               5                  10                  15

Ala

<210> SEQ ID NO 20
<211> LENGTH: 9
<212> TYPE: PRT
<213> ORGANISM: Mus musculus

<400> SEQUENCE: 20

Gly Leu Arg Leu Arg Phe Phe Asp Tyr
 1               5

<210> SEQ ID NO 21
<211> LENGTH: 10
<212> TYPE: PRT
<213> ORGANISM: Mus musculus

<400> SEQUENCE: 21

Ser Ala Ser Ser Ser Val Ser Tyr Met His
 1               5                  10

<210> SEQ ID NO 22
<211> LENGTH: 7
<212> TYPE: PRT
<213> ORGANISM: Mus musculus

<400> SEQUENCE: 22

Asp Thr Ser Lys Leu Ala Ser
 1               5

<210> SEQ ID NO 23
<211> LENGTH: 10
<212> TYPE: PRT
<213> ORGANISM: Mus musculus

<400> SEQUENCE: 23

Gln Gln Trp Ser Ser Asn Pro Pro Ile Thr
 1               5                  10

<210> SEQ ID NO 24
<211> LENGTH: 5
<212> TYPE: PRT
<213> ORGANISM: Mus musculus

<400> SEQUENCE: 24

Asp Tyr Gly Met Ala
 1               5

<210> SEQ ID NO 25
<211> LENGTH: 17
<212> TYPE: PRT
<213> ORGANISM: Mus musculus

<400> SEQUENCE: 25

Ala Ile Ser Ser Gly Gly Ser Tyr Ile His Phe Pro Asp Ser Leu Lys
 1               5                  10                  15

Gly
```

```
<210> SEQ ID NO 26
<211> LENGTH: 12
<212> TYPE: PRT
<213> ORGANISM: Mus musculus

<400> SEQUENCE: 26

Arg Gly Phe Tyr Gly Asn Tyr Arg Ala Met Asp Tyr
 1               5                  10

<210> SEQ ID NO 27
<211> LENGTH: 15
<212> TYPE: PRT
<213> ORGANISM: Mus musculus

<400> SEQUENCE: 27

Arg Ala Asn Glu Ser Val Asp His Asn Gly Val Asn Phe Met Asn
 1               5                  10                  15

<210> SEQ ID NO 28
<211> LENGTH: 7
<212> TYPE: PRT
<213> ORGANISM: Mus musculus

<400> SEQUENCE: 28

Ala Ala Ser Asn Gln Gly Ser
 1               5

<210> SEQ ID NO 29
<211> LENGTH: 9
<212> TYPE: PRT
<213> ORGANISM: Mus musculus

<400> SEQUENCE: 29

Gln Gln Ser Lys Asp Val Pro Trp Thr
 1               5
```

REMEDY FOR ENDOMETRIOSIS

TECHNICAL FIELD

The present invention relates to a therapeutic agent for endometriosis which comprises an interleukin-5 (hereinafter abbreviated as IL-5) antagonist as an active ingredient.

BACKGROUND ART

A method for treating endometriosis is mainly classified into pharmacotherapy and surgical therapy. As pharmacotherapy, symptomatic treatment such as analgesic agents and pills and hormone therapy such as administration of an agent for treating endometriosis are included. Surgical therapy includes conservative surgery, radical operation and the like (non-Patent Document 1). However, even these surgical therapies have been insufficient in some cases and thus an agent to completely cure endometriosis has not been developed so far.

As an antibody which specifically reacts with human IL-5, SB-240563 (Smithkline-Beecham), Sch-55700 (CDP-835; Schering-Plough/Celltech), and the like have been known. SB-240563 shows an activity to reduce the number of eosinophils in peripheral blood of patients with slight degree of asthma (10$^{th}$ *Annual Meetings of the America Society for Clinical Pharmacology and Therapeutics*, March, 1999). Sch-55700 has been known to suppress increase of eosinophils in lung which is caused by priming in the simian models for allergic diseases (Non-patent document 2).

Further, as the antibody which reacts with IL-5 receptor a chain, humanized antibody KM8399 is known (Patent document 1). KM8399 is expected to be useful as a therapeutic agent for allergic diseases such as chronic bronchial asthma. It is also known that KM8399 has Fc region of human IgG1 subclass and it specifically induces apoptosis human eosinophils, and apoptosis is induced by antibody-dependent cytotoxic activity (Patent Document 2).

However, the relation between an antibody which specifically binds to human IL-5 or an antibody which specifically binds to a human IL-5 receptor mentioned above and endometriosis has not been known.

Non-patent Document 1: Tsutomu Douchi et al., Selection of Treatment of Endometriosis, *Gynecologic Therapy*, 78, 179-182 (1999)

Non-patent Document 2: *Arzneimittel-Forschung*, 49, 779 (1999)

Patent Document 1: WO97/10354
Patent Document 2: WO01/60405

DISCLOSURE OF THE INVENTION

Problems to be Solved by the Invention

An agent useful for treating endometriosis has been demanded.

Means for Solving the Problems

The present invention relates to the following (1) to (13):
(1) A therapeutic agent for endometriosis which comprises an interleukin-5 antagonist as an active ingredient.
(2) The therapeutic agent according to (1), wherein the interleukin-5 antagonist is an antibody which inhibits the binding of interleukin-5 to an interleukin-5 receptor or an antibody fragment thereof.
(3) The therapeutic agent according to (2), wherein the antibody which inhibits the binding of interleukin-5 to an interleukin-5 receptor is an antibody which binds to interleukin-5.
(4) The therapeutic agent according to (3), wherein interleukin-5 is human interleukin-5.
(5) The therapeutic agent according to (2), wherein the antibody which inhibits the binding of interleukin-5 to an interleukin-5 receptor is an antibody which binds to an interleukin-5 receptor.
(6) The therapeutic agent according to (5), wherein the interleukin-5 receptor is interleukin-5 receptor a chain.
(7) The therapeutic agent according to (5) or (6), wherein the interleukin-5 receptor is a human interleukin-5 receptor.
(8) The therapeutic agent according to any one of (2) to (7), wherein the antibody is a monoclonal antibody.
(9) The therapeutic agent according to (8), wherein the monoclonal antibody is a gene recombinant antibody.
(10) The therapeutic agent according to (9), wherein the gene recombinant antibody is a gene recombinant antibody selected from the group consisting of a human chimeric antibody, a humanized antibody and a human antibody.
(11) The therapeutic agent according to any one of (2) to (10), wherein the antibody fragment is an antibody fragment selected from Fab, Fab', F(ab')$_2$, single chain antibody (scFv), dimerized variable region (Diabody), disulfide stabilized variable region (dsFv) and a peptide comprising CDR.
(12) Use of the interleukin-5 antagonist described in any one of (1) to (11), for the manufacture of a therapeutic agent for endometriosis.
(13) A method for treating endometriosis which comprises administering the interleukin-5 antagonist described in any one of (1) to (11).

Effect of the Invention

The present invention provides a therapeutic agent for endometriosis comprising an IL-5 antagonist as an active ingredient.

BRIEF DESCRIPTION OF THE DRAWINGS

FIG. 1 shows an activity of anti-mouse IL-5 receptor antibody to suppress the formation of endometriotic lesions in mouse model of endometriosis. The ordinate shows the lesion size (mm$^2$).

FIG. 2 shows an activity of anti-mouse IL-5 antibody to suppress the formation of endometriotic lesions in mouse model of endometriosis. The ordinate shows the lesion size (mm$^2$).

BEST MODE FOR CARRYING OUT THE INVENTION

The IL-5 antagonist used in the present invention may be any antagonist as long as it blocks the signal transduction between IL-5 and an IL-5 receptor and inhibits biological activity of IL-5, and it may have a low molecular weight or a high molecular weight. For example, it includes an antibody which inhibits the binding of IL-5 to an IL-5 receptor or an antibody fragment thereof.

An antibody which inhibits the binding of IL-5 to the IL-5 receptor includes an antibody which binds to IL-5 and which inhibit the binding of IL-5 to the IL-5 receptor, an antibody which binds to IL-5 receptor and which inhibit the binding of IL-5 to the IL-5 receptor, and the like. As the IL-5 receptor, an IL-5 receptor α chain, an IL-5 receptor β chain and the like can be included.

The aforementioned antibody or the antibody fragment thereof used in the present invention may be any of a polyclonal antibody or a monoclonal antibody, and a monoclonal antibody is preferred.

A monoclonal antibody includes a hybridoma-producing antibody, a gene recombinant antibody, and the like.

A hybridoma is a cell which is obtained by cell fusion between a B cell obtained by immunizing a non-human mammal with an antigen and a myeloma cell and which can produce a monoclonal antibody having the desired antigen specificity.

Examples of the gene recombinant antibody include a human chimeric antibody, a humanized antibody, a human antibody, and the like.

The human chimeric antibody refers to an antibody comprising VH and VL of an antibody of the non-human animal and CH and CL of a human antibody. As CH of the human chimeric antibody, any CH may be used so long as it belongs to human immunoglobulin (hereinafter, referred to as hIg), that of a hIgG class is preferred. Any of subclasses hIgG1, hIgG2, hIgG3 and hIgG4 belonging to a hIgG class may be used as well. With regard to CL of the human chimeric antibody, any CL may be used so long as it belongs to hIg and any of a κ class and a λ class may be used.

The non-human animals include mouse, rat, hamster, rabbit and the like.

The humanized antibody is an antibody in which CDRs of VH and VL of a non-human animal antibody are grafted into an appropriate position in VH and VL of a human antibody, and also referred to as a human CDR-grafted antibody.

The humanized antibody of the present invention can be produced by designing and constructing cDNAs encoding V regions in which CDRs of VH and VL of a non-human animal antibody are ligated to the frameworks (hereinafter referred to as FR(s)) of VH and VL of any human antibody, inserting them into an expression vector for an animal cell having cDNAs encoding CH and CL of a human antibody, respectively, to thereby construct a humanized antibody expression vector, and then introducing the expression vector into an animal cell to express the humanized antibody.

As the CH of a humanized antibody, any CH can be used so long as it belongs to the hIg, however, those belonging to the hIgG class are preferred and any one of the subclasses belonging to the hIgG class such as hIgG1, hIgG2, hIgG3 and hIgG4 can be used. Further, as the CL of a humanized antibody, any CL can be used so long as it belongs to the hIg, and those belonging to a κ class or a λ class can be used.

Although the human antibody is originally an antibody existing naturally in human body, it also includes an antibody which is obtained from a human antibody phage library and from human antibody-producing transgenic animals prepared by the recent advance in genetic engineering, cell engineering and developmental engineering techniques. Regarding the antibody existing in the human body, for example, by isolating a human peripheral blood lymphocyte, immortalizing it by its infection with EB virus or the like and then cloning it to thereby obtain lymphocytes capable of producing the antibody, culturing the lymphocytes thus obtained, and purifying the antibody from the culture supernatant. The human antibody phage library is a library in which antibody fragments such as Fab and scFv are expressed on the phage surface by inserting a gene encoding the antibody prepared from human B cell into a phage gene. A phage expressing antibody fragments having the desired antigen binding activity on the surface can be collected from the library using the binding activity to an antigen-immobilized substrate as an index. The antibody fragments can be further converted into a human antibody molecule comprising two full length H chains and two full length L chains by genetic engineering techniques. The human antibody-producing transgenic animal means an animal in which a human antibody gene is integrated into its cells. For example, a human antibody-producing transgenic mouse can be prepared by introducing a human antibody gene into a mouse ES cell, transplanting the ES cell into early embryo of a mouse and then developing. Regarding the method for preparing a human antibody from a human antibody-producing transgenic animal, the human antibody can be formed and accumulated in a culture supernatant by culturing a human antibody-producing hybridoma obtained by a hybridoma preparation method generally carried out in non-human animal.

The antibody or the antibody fragment which is preferably used in the present invention includes a monoclonal antibody produced by hybridoma ATCC HB10959 (Japanese Published Unexamined Patent Application No. 2000-210097) which binds to IL-5 and which inhibits the binding of IL-5 to an IL-5 receptor; a monoclonal antibody produced by hybridoma KM1259 (FERM BP-5134, WO97/10354) and hybridoma KM1486 (FERM BP-5651, WO97/10354) and the like, which binds to IL-5 receptor α chain and inhibits the binding of IL-5 to an IL-5 receptor; and a monoclonal antibody produced by hybridoma BION-1 (ATCC HB-12525, WO00/09561) which specifically binds to IL-5 receptor β chain and which inhibits the binding of IL-5 to an IL-5 receptor, and the antibody fragments thereof.

Specific examples of the human chimeric antibody which binds to a human IL-5 receptor and which inhibits the binding of IL-5 to an IL-5 receptor include an anti-human IL-5R α chain chimeric antibody which comprises: CDR1, CDR2 and CDR3 of VH comprising the amino acid sequences represented by SEQ ID NOs:1, 2 and 3, respectively, and/or CDR1, CDR2 and CDR3 of VL comprising the amino acid sequences represented by SEQ ID NOs:4, 5 and 6, respectively; an anti-human IL-5 α chain chimeric antibody comprising VH of antibody comprising the amino acid sequence represented by SEQ ID NO:7 and/or VL of antibody comprising the amino acid sequence represented by SEQ ID NO:8; an anti-human IL-5R α chain chimeric antibody comprising VH of antibody comprising the amino acid sequence represented by SEQ ID NO:7 and CH of human antibody comprising an amino acid sequence of the hIgG1 subclass and VL of antibody comprising the amino acid sequence represented by SEQ ID NO:8 and CL of the human antibody comprising an amino acid sequence of the K class. Examples include KM 1399 (WO97/10354), and the like.

Examples of the humanized antibody which binds to a human IL-5 receptor a chain and which inhibits the binding of IL-5 to an IL-5 receptor include an antibody which comprises: CDR1, CDR2 and CDR3 of VH comprising the amino acid sequences represented by SEQ ID NOs:24, 25 and 26, respectively, and/or CDR1, CDR2 and CDR3 of VL comprising the amino acid sequences represented by SEQ ID NOs:27, 28 and 29, respectively; more preferably, an antibody which comprises: CDR1, CDR2 and CDR3 of VH comprising the amino acid sequences represented by SEQ ID NOs:18, 19 and 20, respectively, and/or CDR1, CDR2 and CDR3 of VL comprising the amino acid sequences represented by SEQ ID NOs:21, 22 and 23, respectively; still more preferably an antibody which comprises: CDR1, CDR2 and CDR3 of VH of antibody comprising the amino acid sequences represented by SEQ ID NOs:1 2 and 3, respectively, and/or CDR1, CDR2 and CDR3 of VL comprising the amino acid sequences represented by SEQ ID NOs:4, 5 and 6, respectively, and the antibody fragments thereof.

Among the above humanized antibody, a humanized antibody which comprises VH of the antibody in which an amino acid sequence represented by SEQ ID NO:9 or at least one amino acid residue selected from Ala at position 40, Glu at position 46, Arg at position 67, Ala at position 72, Thr at position 74, Ala at position 79, Tyr at position 95 and Ala at position 97 in the amino acid sequence represented by SEQ ID NO:9 is replaced with another amino acid residue and a humanized antibody which comprises VL of the antibody in which an amino acid sequence represented by SEQ ID NO: 10 or at least one amino acid residue selected from Ser at position 7, Pro at position 8, Thr at position 22, Gln at position 37, Gln at position 38, Pro at position 44, Lys at position 45, Phe at position 71, Ser at position 77, Tyr at position 87 and Phe at position 98 in the amino acid sequence represented by SEQ ID NO:10 is replaced with another amino acid residue are preferred; a humanized antibody which comprises VH of the antibody in which at least one amino acid residue selected from Ala at position 40, Glu at position 46, Arg at position 67, Ala at position 72, Thr at position 74, Ala at position 79, Tyr at position 95 and Ala at position 97 in the amino acid sequence represented by SEQ ID NO:9 is replaced with another amino acid residue and VL of the antibody in which at least one amino acid residue selected from Ser at position 7, Pro at position 8, Thr at position 22, Gln at position 37, Gln at position 38, Pro at position 44, Lys at position 45, Phe at position 71, Ser at position 77, Tyr at position 87 and Phe at position 98 in the amino acid sequence represented by SEQ ID NO:10 is replaced with another amino acid residue are more preferred.

Examples include a humanized antibody which comprises:
an amino acid sequence in which VH of antibody is represented by SEQ ID NO:9, 11, 12 and 13, respectively or an amino acid in which at least one amino acid residue selected from Ala at position 40, Glu at position 46, Arg at position 67, Ala at position 72, Thr at position 74, Ala at position 79, Tyr at position 95 and Ala at position 97 in the amino acid sequence represented by SEQ ID NO:9 is replaced with another amino acid residue, and/or
an amino acid sequence in which VL of antibody is represented by SEQ ID NO:10, 14, 15, 16 and 17, respectively; or an amino acid in which at least one amino acid residue selected from Ser at position 7, Pro at position 8, Thr at position 22, Gln at position 37, Gln at position 38, Pro at position 44, Lys at position 45, Phe at position 71, Ser at position 77, Tyr at position 87 and Phe at position 98 in the amino acid sequence represented by SEQ ID NO:10 is replaced with another amino acid residue. More specifically, a humanized antibody comprising amino acid sequences in which VH is represented by SEQ ID NO:13 and VL is represented by SEQ ID NO:10, for example, KM8399 (WO97/10354), KM7399 (WO97/10354) and the like is included.

Further, a humanized antibody which binds to IL-5 and which inhibit the binding of IL-5 to an IL-5 receptor includes mepolizumab [SB-240563; manufactured by GlaxoSmithKline], reslizumab [Sch-55700; manufactured by Schering-Plough/Celltech], and the like.

In the amino acid sequences constituting the above antibody or antibody fragment, the antibody or antibody fragment in which one or more amino acid residue(s) is/are deleted, added, substituted or inserted and which has an activity substantially equal to the antibody or antibody fragment mentioned above is included in the antibody used in the present invention.

Number of the amino acid to be deleted, substituted, inserted or added is one and more, and the number is not particularly limited, but is a number which can be deleted, substituted or added by a known technique such as site-directed mutagenesis, described in *Molecular Cloning, A Laboratory Manual*, Second Edition; *Current Protocols in Molecular Biology*; *Nucleic Acids Research*, 10, 6487 (1982); *Proc. Natl. Acad. Sci. USA*, 79, 6409 (1982); *Gene*, 34, 315 (1985); *Nucleic Acids Research*, 13, 4431 (1985); *Proc. Natl. Acad. Sci. USA*, 82, 488 (1985), and the like. For example, it is 1 to several tens, preferably 1 to 20, more preferably 1 to 10, and further preferably 1 to 5.

One or more amino acid deleted substituted, inserted or added in the amino acid sequence of the above antibody means that one or plurality of amino acid(s) is/are deleted, substituted, inserted or added to at one or plural arbitrary position(s) in the amino acid sequence. The deletion, substitution, insertion or addition may be carried out in the same amino acid sequence simultaneously. Also, the amino acid residue substituted, inserted or added can be natural or non-natural. The natural amino acid residue includes L-alanine, L-asparagine, L-aspartic acid, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine, L-valine, L-cysteine and the like.

Thereinafter, preferred examples of amino acid residues which are capable of substituting one another are shown. The amino acid residues in the same group can be substituted with each other.

Group A: leucine, isoleucine, norleucine, valine, norvaline, alanine, 2-aminobutanoic acid, methionine, O-methylserine, t-butylglycine, t-butylalanine, cyclohexylalanine;
Group B: aspartic acid, glutamic acid, isoaspartic acid, isoglutamic acid, 2-aminoadipic acid, 2-aminosuberic acid;
Group C: asparagine, glutamine;
Group D: lysine, arginine, ornithine, 2,4-diaminobutanoic acid, 2,3-diaminopropionic acid;
Group E: proline, 3-hydroxyproline, 4-hydroxyproline;
Group F: serine, threonine, homoserine;
Group G: phenylalanine, tyrosine.

The antibody fragment used in the present invention includes Fab, Fab', F(ab')$_2$, scFv, diabody, dsFv, a peptide comprising CDR, and the like.

Fab is an antibody fragment having a molecular weight of about 50,000 and having an antigen binding activity where about a half of N-terminal side of H chain and the full length of L chain, among fragments obtained by treating IgG-type antibody molecule with a protease, papain (cleaving an amino acid residue at position 224 of an H chain) are bound together through a disulfide bond.

The Fab used in the present invention can be produced by treating the antibody with a protease, papain. Alternatively, DNA encoding Fab of the antibody is inserted into expression vector for prokaryote or expression vector for eukaryote and the vector is introduced into prokaryote or eukaryote to induce expression.

F(ab')$_2$ is an antibody fragment having a molecular weight of about 100,000 and having an antigen binding activity which is slightly larger than the Fab bound via disulfide bond of the hinge region, among fragments obtained by treating IgG-type antibody molecule with a protease, pepsin.

The F(ab')$_2$ used in the present invention can be prepared by treating the antibody with a protease, pepsin. Alternatively, it can be prepared by linking Fab' described below via a thioether bond or a disulfide bond.

Fab' is an antibody fragment having a molecular weight of about 50,000 and having an antigen binding activity where a disulfide bond at a hinge region of the aforementioned F(ab')$_2$ is cleaved.

The Fab' used in the present invention can be prepared by treating F(ab')$_2$ with a reducing agent, dithiothreitol. Alternatively, DNA encoding Fab' fragment of the antibody is inserted into an expression vector for prokaryote or an expression vector for eukaryote and the vector is introduced into the prokaryote or the eukaryote to induce expression.

scFv is an antibody fragment having an antigen binding activity and is an VH-P-VL or an VL-P-VH polypeptide where one VH and one VL are linked using an appropriate peptide linker (hereinafter, referred to as P).

The scFv used in the present invention can be produced in such a manner that cDNA encoding VH and VL of the antibody is obtained, DNA encoding scFV is constructed, the DNA is inserted into an expression vector for prokaryote or expression vector for eukaryote and the expression vector is introduced into the prokaryote or the eukaryote to induce expression.

Diabody is an antibody fragment where svFv is dimerized and is an antibody fragment having divalent antigen binding activity. The divalent antigen binding activity may be the same or one of them can be used as a different antigen binding activity.

The diabody used in the present invention can be produced in such a manner that cDNA encoding VH and VL of antibody is obtained, DNA encoding scFv is constructed so as to make the length of amino acid sequence of the linker to be not more than 8 residues, the DNA is inserted into expression vector for prokaryote or expression vector for eukaryote and the expression vector is introduced into the prokaryote or the eukaryote to induce expression.

The dsFv is an antibody fragment where a polypeptide in which each one amino acid residue in VH and VL is substituted with a cysteine residue is linked via a disulfide bond between the cysteine residues. The amino acid residue to be substituted with a cysteine residue can be selected based on a three-dimensional structure estimation of the antibody according to a method shown by Reiter, et al. (*Protein Engineering*, 7, 697-704 (1994)).

The dsFv used in the present invention can be produced in such a manner that cDNA encoding VH and VL of an antibody is obtained, DNA encoding the dsFv is constructed, the DNA is inserted into expression vector for prokaryote or expression vector for eukaryote and the expression vector is introduced into the prokaryote or the eukaryote to induce expression.

A peptide comprising CDR is constituted by comprising at least one region of CDRs of VH or VL. A peptide comprising plural CDRs can be linked either directly or via an appropriate peptide linker. A peptide comprising CDR used in the present invention can be produced in such a manner that DNA encoding VH and VL of an antibody is constructed, the DNA is inserted into expression vector for prokaryote or expression vector for eukaryote and the expression vector is introduced into the prokaryote or the eukaryote to induce expression. The peptide comprising CDR can also be prepared by a chemical synthetic method such as an Fmoc method (fluorenylmethyloxycarbonyl method) and a tBoc method (tert-butyloxycarbonyl method).

A process for producing the antibody or the antibody fragment used in the present invention and evaluation of activity thereof will be mentioned below.

1. Preparation of Monoclonal Antibody
(1) Preparation of Antigen

An expression vector comprising cDNA encoding polypeptide which is an antigen is introduced and expressed in *Escherichia coli*, yeast, insect cell, animal cell, and the like to thereby obtain recombinant protein and the resulting protein can be used as an antigen. Alternatively, a synthetic peptide having a partial amino acid sequence of polypeptide of antigen can also be used as an antigen.

With regard to a partial peptide for antigen, a partial protein sequence of about 5 to 30 residues is selected. In order to obtain an antibody which recognizes the protein in a state of having a non-denatured natural structure, it is necessary to select a partial amino acid sequence existing on the surface of protein in view of three-dimensional structure as an antigen peptide. An example of the method for analyzing the three-dimensional structure of the protein includes a method which predicts a highly hydrophilic partial sequence using commercially available software for analysis of protein sequence such as Genetyx Mac, and the like. There are many cases where a lowly hydrophilic region is present in the inner part of the protein in view of three-dimensional structure and there are many cases where a highly hydrophilic region is present on the surface of protein. In addition, there are many cases where N-terminal and C-terminal of protein are present on the surface of protein.

In order to cross-link to protein, cysteine is added to the terminal of a partial peptide. When an internal sequence of protein is selected as a partial peptide, N-terminal and C-terminal of the peptide are acetylated and amidated, respectively, if necessary. A partial peptide can be synthesized by a common liquid-phase or solid-phase peptide synthetic method, a method where they are appropriately combined or a modified method thereof (*The Peptides, Analysis, Synthesis, Biology*, Vol. 1 (1979); Vol. 2 (1980); Vol. 3, (1981), Academic Press; *Fundamentals and Experiments for Peptide Synthesis*, Maruzen (1985); *Development of Drugs*, Second Series, Vol. 14, Peptide Synthesis, Hirokawa Shoten (1991); *International Journal of Protein & Protein Research*, 35, 161-214 (1990)). It is also possible to use an automated peptide synthesizer. Synthesis of peptide using a peptide synthesizer can be carried out on a commercially available peptide synthesizer such as a peptide synthesizer manufactured by Shimadzu, a peptide synthesizer manufactured by Applied Biosystems, Inc. (hereinafter, referred to as ABI) and a peptide synthesizer manufactured by Advanced ChemTech Inc. (hereinafter, referred to as ACT) using Nα-Fmoc-amino acid or Nα-Boc-amino acid where side chain is appropriately protected according to synthetic program for each of them.

Protected amino acids used as raw material and carrier resins are available from ABI, Shimadzu, Kokusan Kagaku, Nova Biochem, Watanabe Kagaku, ACT, Peptide Laboratory, etc. Protected amino acids, protected organic acids and protected organic amines used as starting materials may also be synthesized by already-reported synthetic methods or modified methods thereof (*The Peptides, Analysis, Synthesis, Biology*, Vol. 1 (1979); Vol. 2 (1980); Vol. 3 (1981), Academic Press; *Fundamentals and Experiments for Peptide Synthesis*, Maruzen (1985); *Development of Drugs*, Second Series, Vol. 14, Peptide Synthesis, Hirokawa Shoten (1991); *International Journal of Protein & Protein Research*, 35, 161-214 (1990)).

(2) Immunization of Animal and Preparation of Antibody-Producing Cell

With regard to the animal used for immunization, any animals may be used so long as it can prepare hybridoma such as mouse, rat, hamster and rabbit Examples using mouse and rat will be illustrated below.

3 to 20-week-old mice or rats were immunized with the antigen which is prepared in aforementioned 1(1) and antibody-producing cells are collected from spleen, lymph node and peripheral blood of the animal. Immunization is carried out by administering an antigen to the animal for several times together with an appropriate adjuvant subcutaneously, intravenously or intraperitoneally. Examples of the adjuvant include complete Freund's adjuvant or aluminum hydroxide gel, pertussis vaccine and the like. A conjugate is prepared with carrier protein such as bovine serum albumin (hereinafter, referred to as BSA) or keyhole limpet hemocyanin (hereinafter, referred to as KLH) and the resulting conjugate can be used as an immunogen. After 3 to 7 days from administrating each antigen, blood is collected from venous plexus of fundus of the eye or tail vein of the immunized animal, its reactivity to an antigen is confirmed by means of ELISA or the like and the mouse or rat where its serum shows a sufficient antibody value is used as a source for antibody-producing cell. On the 3 to 7 days from the final administration of the antigen, spleen, etc. are excised from the immunized mouse or rat according to a known method (*Antibodies—A Laboratory Manual*, Cold Spring Harbor Laboratory (1988)) and antibody-producing cells and myeloma cells are fused.

(3) Preparation of Myeloma Cell

With regard to the myeloma cell, any myeloma cell may be used so long as it can proliferate in vitro such as 8-azaguanine-resistant myeloma cell line P3-X63Ag8-U1 (P3-U1) (*European Journal of Immunology*, 6, 511-519 (1976)), SP2/0-Ag14 (SP-2) (*Nature*, 276, 269-270 (1978)), P3-X63-Ag8653 (653) (*Journal of Immunology*, 123, 1548-1550 (1979)), P3-X63-Ag8 (X63) (*Nature*, 256, 495-497 (1975)) or the like. The culturing and sub-culturing of those cell lines can be carried out in accordance with a known method (*Antibodies—A Laboratory Manual*, Cold Spring Harbor Laboratory (1988) to thereby secure not less than $2 \times 10^7$ cells until the stage of cell fusion.

(4) Cell Fusion

The antibody-producing cell and myeloma cell prepared hereinabove are washed and a cell-aggregating medium such as polyethylene glycol-1000 (hereinafter, referred to as PEG-1000) is added thereto whereupon cells are fused and suspended in a medium. For washing the cells, modified Eagle's medium (hereinafter, referred to as MEM), phosphate buffered saline (hereinafter, referred to as PBS) or the like is used. With regard to a medium in which the fused cells are suspended, an HAT medium {a medium where 0.1 mM hypoxanthine, 15 μM thymidine and 0.4 μM aminopterin are added to a common medium [a medium where 1.5 mM glutamine, 50 μM 2-mercaptoethanol, 10 μg/mL gentamicin and 10% fetal bovine serum (hereinafter, referred to as FBS) are added to an RPMI-1640 medium]} is used so that the desired fused cell is selectively obtained.

After the culturing, a part of the culture supernatant liquid is taken out and a sample which reacts with antigen protein and does not react with non-antigen protein is selected by ELISA. After that, a limiting diluting method is carried out to make it into a single cell and a sample which showed a stable and high antibody titer by ELISA is selected as a monoclonal antibody-producing hybridoma.

(5) Selection of Hybridoma

Selection of hybridoma which produces an antigen-reacting antibody is carried out by ELISA which will be mentioned later in accordance with a known method (*Antibodies—A Laboratory Manual*, Cold Spring Harbor Laboratory (1988)). According to such a method, it is now possible to measure a binding activity of an antigen of antibody contained in a culture supernatant of transformant cell line which produces human chimeric antibody, CDR-grafted antibody or antibody fragment thereof or antibody purified from the culture supernatant which will be mentioned later.

ELISA

Antigen is fixed in a 96-well ELISA plate and reaction is carried out using a culture supernatant of such as a hybridoma or a purified antibody as the first antibody. After the reaction of the first antibody, the plate is washed and the second antibody is added. With regard to the second antibody, an antibody which can recognize the first antibody is labeled with biotin, enzyme, chemiluminescent substance, radioisotope or the like is used. To be more specific, when a mouse is used in the preparation of the hybridoma, an antibody which can recognize the mouse antibody is used as the second antibody. After the reaction, the reaction corresponding to the labeled substance of the second antibody is carried out to select a hybridoma producing a monoclonal antibody which specifically reacts with the antigen.

(6) Purification of Monoclonal Antibody

The monoclonal antibody-producing hybridoma cell obtained in 1(4) is intraperitoneally injected in an amount of $5 \times 10^6$ to $2 \times 10^7$ cells/mouse to a mouse or nude mouse of 8 to 10 weeks old to which 0.5 mL of pristane (2,6,10,14-tetramethylpentadecane) is intraperitoneally administered, followed by breeding for two weeks. With 10 to 21 days, the hybridoma becomes ascites tumor. The ascites is collected from the mouse or nude mouse, centrifuged, salting out with 40 to 50% saturated ammonium sulfate, subjected to a precipitation method with caprylic acid and IgG or IgM fraction is recovered by using DEAE-Sepharose column, protein A column, column of Cellulofine GSL 2000 (manufactured by Seikagaku Kogyo) or the like to prepare purified monoclonal antibody.

The subclass of the purified monoclonal antibody can be determined by using a mouse monoclonal antibody typing kit, a rat monoclonal antibody typing kit or the like. Concentration of protein can be calculated by a Lowry method or from the absorbance at 280 nm.

The subclass of the antibody means an isotype in the class and includes IgG1, IgG2a, IgG2b and IgG3 in the case of mouse and IgG1, IgG2, IgG3 and IgG4 in the case of human.

(7) Activity Evaluation of Monoclonal Antibody (7-1) Evaluation of Binding Activity to Antigen Binding activity of the monoclonal antibody which is in a culture supernatant or is purified from the culture supernatant to antigen can be measured by ELISA in aforementioned 1(5), surface plasmon resonance (*Journal of Immunological Methods*, 145, 229-240 (1991)), and the like. Reactivity with antigen and antigen epitope can also be analyzed by a competitive ELISA using antigen peptide and partial peptides thereof. It can be presumed by a commonly conducted three-dimensional structural analytical method or combination of various immunological methods whether the antibody recognizes the three-dimensional structure of the protein which is an antigen. Examples of the three-dimensional structural analytical method include X-ray crystallography and nuclear magnetic resonance method. Examples of a combination of various immunological methods include a combination of ELISA to non-denatured antigen and ELISA to denatured antigen. In that case, the antibody having reactivity only to non-denatured antigen is highly presumed that it recognizes the three-dimensional structure of the antigen. Examples of ELISA to non-denatured antigen include ELISA where non-denatured antigen is allowed to react with antibody in a liquid phase. With regard to ELISA to denatured antigen, any method may be used so long as it is ELISA in which antibody is made to react under such a state that antigen does not have its natural three-dimensional structure and examples include ELISA to an antigen which is directly fixed on a hydrophobic reaction plate and to partial peptide which is digested into an appropriate length.

2. Preparation of Polyclonal Antibody of Non-Human Animal to Antigen

A polyclonal antibody can be prepared from serum of an animal where its serum shows a sufficient antibody titer among the animal to which immune is applied by the above method mentioned in 1.(2).

Thus, the serum fractionated by a centrifugation from the blood recovered from the animal and the immunoglobulin fraction is purified from the serum by a conventional method whereupon the polyclonal antibody can be prepared. With regard to activity of the polyclonal antibody, a binding activity to antigen can be evaluated by the above method mentioned in 1.(7).

3. Preparation of Human Chimeric Antibody and Humanized Antibody (1) Construction of Vector for Expression of Human Chimeric Antibody and Humanized Antibody With regard to a vector for expression of human chimeric antibody and humanized antibody (hereinafter, both of which are referred to as a vector for expression of humanized antibody), any vector for expression of humanized antibody may be used so long as it is an expression vector for animal cell into which gene encoding CH and/or CL of human antibody is inserted. A expression vector for expression of humanized antibody can be constructed by cloning the genes encoding CH and CL of human antibody, respectively, into expression vector for animal cell.

C region of human antibody may be CH and CL of any human antibody and examples include C region of IgG1 subclass of H chain of human antibody (hereinafter, referred to as hCγ1), C region of K class of L chain of human antibody (hereinafter, referred to as hCκ) and the like. With regard to the genes encoding CH and CL of human antibody, a chromosome DNA comprising exon and intron may be used and also, cDNA may be used.

With regard to expression vector for animal cell, any vector may be used so long as the gene encoding the C region of human antibody can be inserted and expressed. Examples include pAGE107 (*Cytotechnology*, 3, 133-140 (1990)), pAGE103 (*Journal of Biochemistry*, 101, 1307-1310 (1987)), pHSG274 (Gene, 27, 223-232 (1984)), pKCR (*Proceedings of the National Academy of Sciences of the United State of America*, 78, 1527-1531 (1981)), pSG1βd2-4 (*Cytotechnology*, 4, 173-180 (1990)) and the like. Examples of promoter and enhancer used for the expression vector for animal cells include SV40 initial promoter and enhancer (*Journal of Biochemistry*, 101, 1307-1310 (1987)), Moloney mouse leukemia virus LTR promoter and enhancer (*Biochemical & Biophysical Research Communications*, 149, 960-968 (1987)), immunoglobulin H chain promoter (*Cell*, 41, 479-487 (1985)) and enhancer (*Cell*, 33, 717-728 (1983)) and the like.

With regard to the vector for expression of humanized antibody, either of a type where antibody H chain and L chain are on different vectors and where they are on the same vector (hereinafter, referred to as a tandem type) may be used but, in view of easiness of construction of human chimeric antibody expression vector and humanized antibody expression vector, easiness of introduction into animal cells and well-balanced expressed amount of antibody H chain and L chain in animal cells, a tandem type of vector for expression of humanized antibody is preferred (*Journal of Immunological Methods*, 167, 271-278 (1994)). Examples of a tandem type of vector for expression of humanized antibody include pKANTEX93 (WO 97/10354), pEE18 (*Hybridoma*, 17, 559-567 (1998)) and the like.

The constructed vector for expression of humanized antibody can be used for expression of human chimeric antibody and humanized antibody in animal cell.

(2) Obtaining of cDNA Encoding V Region of Antibody of Non-Human Animal and Analysis of Amino Acid Sequence Thereof cDNA which encodes antibody of non-human animal such as VH and VL of mouse antibody is obtained as follows.

mRNA is extracted from hybridoma and cDNA is synthesized. The synthesized cDNA is cloned into vector such as plasmid or phage to prepare a cDNA library. Using C region or V region of the mouse antibody as a probe, each of recombinant phage or recombinant plasmid having cDNA encoding VH and recombinant phage or recombinant plasmid having cDNA encoding VL is isolated from the library. Full length of nucleotide sequences of VH and VL of the desired mouse antibody on the recombinant phage or recombinant plasmid are determined and the full length of the amino acid sequences of VH and VL are deduced from the nucleotide sequences.

With regard to non-human animals, any animal such as mouse, rat, hamster and rabbit may be used so long as it can prepare a hybridoma.

Examples of a method for preparing the total RNA from hybridoma include a guanidine thiocyanate-cesium trifluoroacetate method (*Methods in Enzymology*, 154, 3-28 (1987)) and the like, and examples of a method for preparing mRNA from the total RNA include an oligo (dT) immobilized cellulose column method (*Molecular Cloning: A Laboratory Manual*, Cold Spring Harbor Lab. Press, New York (1989)) and the like. Examples of a kit for the preparing mRNA from hybridoma include Fast Track mRNA Isolation Kit (manufactured by Invitrogen), Quick Prep mRNA Purification Kit (manufactured by Pharmacia) and the like.

Examples of a method for the synthesizing of cDNA and for preparing cDNA library include a conventional method (*Molecular Cloning: A Laboratory Manual*, Cold Spring Harbor Lab. Press, New York (1989); *Current Protocols in Molecular Biology*, Supplement 1-34) and a method using a commercially available kit such as Super Script™ Plasmid System for cDNA Synthesis and Plasmid Cloning (manufacture by Gibco BRL) and ZAP-cDNA Synthesis Kit (manufactured by Stratagene).

With regard to the vector into which cDNA synthesized using mRNA extracted from the hybridoma as a template is inserted while preparing the cDNA library, any vector may be used so long as the cDNA can be inserted therein. For example, phage or plasmid vector such as ZAP Express (*Strategies*, 5, 58-61 (1992)), pBluescript II SK(+) (*Nucleic Acid Research*, 17, 9494 (1989)), λ ZAP II (manufactured by Stratagene), λ gt 10 and λ gt 11 (DNA Cloning: A Practical Approach, I, 49 (1985)), Lambda BlueMid (manufactured by Clontech), λ ExCell, pT7T3 18U (manufactured by Pharmacia), pcD2 (*Molecular & Cellular Biology*, 3, 280-289 (1983)) and pUC 18 (*Gene*, 33, 103-119 (1985)) may be used.

With regard to *Escherichia coli* into which a cDNA library constructed by phage or plasmid vector is introduced, any *Escherichia coli* may be used so long as the cDNA library can be introduced, expressed and maintained. Examples include XL1-Blue MRF' (*Journal of Biotechnology*, 23, 271-289 (1992)), C600 (*Genetics*, 59, 177-190 (1968)), Y1088 and Y1090 (*Science*, 222, 778-782 (1983)), NM 522 (*Journal of Molecular Biology*, 166, 1-19 (1983)), K 802 (*Journal of Molecular Biology*, 16, 118-133 (1966)), JM 105 (*Gene*, 38, 275-276 (1985)) and the like.

With regard to a method for selecting cDNA clones encoding VH and VL of antibody of non-human animal from cDNA library, it can be selected by a colony hybridization method or a plaque hybridization method (*Molecular Cloning: A Laboratory Manual*, Cold Spring Harbor Lab. Press, New York (1989)) using radioisotope or fluorescence-labeled probe. In addition, cDNAs encoding VH and VL can be prepared by a polymerase chain reaction (hereinafter, referred to as PCR method; *Molecular Cloning: A Laboratory Manual*, Cold Spring Harbor Lab. Press, New York (1989); *Current Protocols in Molecular Biology*, Supplement 1-34) by preparing primer and cDNA synthesized from mRNA or cDNA library as a template.

cDNA selected by the above-mentioned method is cleaved by an appropriate restriction enzyme or the like, cloned into a plasmid vector such as pBluescript SK(-) (manufactured by Stratagene), subjected to a method conventionally used for analysis of nucleotide sequence such as a dideoxy method (*Proceedings of the National Academy of Sciences of the United States of America*, 74, 5463-5467 (1977)) and analyzed by an automatic sequencer (ABI PRISM 377 (manufactured by ABI)) or the like whereupon a nucleotide sequence of the cDNA can be determined.

The full length of amino acid sequences of VH and VL are deduced from the determined nucleotide sequences and compared with the full length of amino acid sequences of VH and VL of known antibody (*Sequences of Proteins of Immunological Interest*, U.S. Dept. Health and Human Services (1991)) whereupon it can be confirmed whether the obtained cDNA encodes the full length of amino acid sequences of VH or VL of the antibody containing a signal sequence for secretion. With regard to the full length of amino acid sequences of VH or VL of the antibody containing the signal sequence length and N-terminal amino acid sequence of the signal sequence can be deduced by comparing it with the full length of amino acid sequences of VH and VL of the known antibody (*Sequences of Proteins of Immunological Interest*, U.S. Dept. Health and Human Services (1991)) and, further, subclass to which they belong can be determined. Also, an amino acid sequence of each CDR of VH and VL can be found by comparing with the amino acid sequences of VH and VL of the known antibody (*Sequences of Proteins of Immunological Interest*, U.S. Dept. Health and Human Services (1991)).

A homology search of sequences such as a BLAST method (*Journal of Molecular Biology*, 215, 403-410 (1990)) to any database such as SWISS-PROT or PIR-Protein can be conducted using the full length of amino acid sequences of VH and VL to examine novelty of the sequence.

(3) Construction of Human Chimeric Antibody Expression Vector cDNAs encoding VH and VL of antibody of non-human animal are cloned in the upstream of genes encoding CH and CL of human antibody of vector for expression of humanized antibody mentioned in the above 3(1) to thereby construct human chimeric antibody expression vector. For example, each cDNA encoding VH and VL of antibody of non-human animal is ligated to synthetic DNA comprising a nucleotide sequence of 3'-terminal of VH and VL of antibody of non-human animal and a nucleotide sequence of 5'-terminal of CH and CL of human antibody and having recognition sequence of an appropriate restriction enzyme at both ends, and cloned so that each of them is expressed in an appropriate form in the upstream of gene encoding CH and CL of human antibody of the vector for expression of humanized antibody mentioned in the above 3(1) to construct human chimeric antibody expression vector. In addition, cDNA encoding VH and VL is amplified by a PCR method using a primer having a recognition sequence of an appropriate restriction enzyme at 5'-terminal using a plasmid containing cDNA encoding VH and VL of antibody of non-human animal as a template and each of them is cloned so that it is expressed in an appropriate form in the upstream of gene encoding CH and CL of human antibody of the vector for expression of humanized antibody mentioned in the above 3(1) to construct human chimeric antibody expression vector.

(4) Construction of cDNA Encoding V Region of Humanized Antibody cDNAs encoding VH and VL of humanized antibody can be constructed as follows. Firstly, amino acid sequence of FRs in VH and VL of human antibody to which the desired amino acid sequences of CDRs in VH and VL of non-human animal are grafted is selected. With regard to the amino acid sequence of FRs in VH and VL of human antibody, any amino acid sequence of FRs in VH and VL of human antibody may be used so long as it is derived from human antibody. Examples thereof include amino acid sequences of FRs in VH and VL of human antibody registered in database such as Protein Data Bank and a consensus amino acid sequence of each subgroup of FRs in VH and VL of human antibody (*Sequences of Proteins of Immunological Interest*, U.S. Dept. Health and Human Services (1991)). In order to prepare a humanized antibody having a sufficient activity, an amino acid sequence having a homology of as high as possible (at least 60% or more) to the amino acid sequence of FRs in VH and VL of antibody of the desired non-human animal among the above is preferably selected. After that, the amino acid sequence of CDRs in VH and VL of the desired non-human animal antibody is grafted to the selected amino acid sequence of FRs in VH and VL of the human antibody to design the amino acid sequences of VH and VL of the humanized antibody. The designed amino acid sequences are converted to nucleotide sequences by considering the frequency of codon usage (*Sequences of Proteins of Immunological Interest*, U.S. Dept. Health and Human Services (1991)) found in the nucleotide sequence of gene of antibody whereupon nucleotide sequences encoding amino acid sequences of VH and VL of the humanized antibody are designed. Based on the designed nucleotide sequences, several synthetic DNAs having a length of about 100 bases are synthesized and a PCR method is carried out by using them. In this case, it is preferred to design six synthetic DNAs for both VH and VL in view of reaction efficiency in the PCR and length of synthesizable DNA.

Further, by introducing a recognition sequence of an appropriate restriction enzyme into 5'-terminal of synthetic DNAs located at both ends, cloning to an expression vector of humanized antibody constructed in the above 3(1) can be carried out easily. After the PCR, the amplified product is cloned into a plasmid such as pBluescript SK(-) (manufactured by Stratagene) and a nucleotide sequence is determined by the method mentioned in the above 3(2) whereupon a plasmid having nucleotide sequences encoding the amino acid sequences of VH and VL of the desired humanized antibody is obtained.

(5) Modification of Amino Acid Sequence of V Region of Humanized Antibody

It has been known that, when a humanized antibody is produced by simply grafting the CDRs in VH and VL of a desired antibody of the non-human animal into FRs in VH and VL of human antibody, antigen binding activity of human CDR-grafted antibody is lower than the original antibody of the non-human animal (*Bio/Technology*, 9, 266-271 (1991)). With regard to the cause thereof, it is considered that, in the original VH and VL of antibody of the non-human animal, not only CDRs but also some amino acid residues of FRs participate in antigen binding activity either directly or indirectly and that, as a result of grafting of CDRs, such amino acid residues change to amino acid residues being different from FRs in VH and VL of the human antibody. In order to solve the problem, it has been conducted in a humanized antibody that, among the amino acid sequence of FRs in VH and VL of human antibody, an amino acid residue which directly relates to binding to the antigen, or amino acid residue which indirectly relates to binding to an antigen by interacting with an amino acid residue in CDRs or by maintaining the three-dimensional structure of an antibody, is identified and that the amino acid residues are modified to amino acid residues found in the original antibody of non-human animal to thereby increase the lowered antigen binding activity (*Bio/Technology*, 9, 266-271 (1991)). In the preparation of humanized antibody, how to efficiently identify the amino acid residues relating to the antigen binding activity in FR is most important, so that the three dimensional structure of an antibody is constructed and analyzed by X-ray crystallography (*Journal of Molecular Biology*, 112, 535-542 (1977)), a computer-modeling (*Protein Engineering*, 7, 1501-1507 (1994)), or the like. Although information of three-dimensional structure of the antibody as such has given much advantageous information to the preparation of humanized antibody, no method for the preparing a humanized antibody which is applicable to any antibodies has been established yet. Therefore, various attempts must be currently be necessary, for example, several modified antibodies are prepared for each antibody and the correlation to each antigen binding activity is examined.

Modification of amino acid residue of FRs in VH and VL of human antibody can be achieved by conducting a PCR method mentioned in the above 3(4) using a synthetic DNA for the modification. With regard to the amplified product after the PCR, its nucleotide sequence is determined by the method mentioned in the above 3(2) whereby it is confirmed that the desired modification has been carried out.

(6) Construction of the Humanized Antibody Expression Vector cDNAs encoding VH and VL of the humanized antibody constructed in the above 3(4) and (5) are cloned to the upstream of genes encoding CH and CL of the human antibody in the vector for expression of the humanized antibody mentioned in the above 3(1) to thereby construct a humanized antibody expression vector.

For example, in the synthetic DNAs used for the construction of VH and VL of the humanized antibody in the above 3(4) and (5), recognition sequences of an appropriate restriction enzyme are introduced into 5'-terminal of the synthetic DNAs located at both ends whereby they can be cloned to the upstream of genes encoding CH and CL of human antibody in the vector for expression of humanized antibody mentioned in the above 3(1) in such a manner that they are expressed in an appropriate form.

(7) A Transient Expression of Human Chimeric Antibody and Humanized Antibody

In order to efficiently evaluate the antigen binding activity of the various human chimeric antibodies and humanized antibodies prepared, a transient expression of human chimeric antibody and humanized antibody can be conducted using the human chimeric antibody expression vector and the humanized antibody expression vector mentioned in the above 3(3) and (6) or the modified expression vector thereof. With regard to a host cell into which the expression vector is introduced, any cell may be used so long as it is a host cell which can express the human chimeric antibody and the humanized antibody. Generally, COS-7 cell (ATCC CRL1651) is used in view of its high expression amount (*Methods in Nucleic Acids Research*, CRC Press, 283 (1991)). The methods for the introducing the expression vector into COS-7 cells are DEAE-dextran method (*Methods in Nucleic Acids Research*, CRC Press, 283 (1991)), a lipofection method (*Proceedings of the National Academy of Sciences of the United States of America*, 84, 7413-7417 (1987)), and the like.

After introducing the expression vector, the amount of human chimeric antibody and humanized antibody expressed in the culture supernatant and antigen binding activity can be measured by, for example, ELISA (*Antibodies: A Laboratory Manual*, Cold Spring Harbor Laboratory, Chapter 14 (1988); *Monoclonal Antibodies: Principles and Practice*, Academic Press Limited (1996)).

(8) Stable Expression of Human Chimeric Antibody and Humanized Antibody

A transformant cell which stably expresses a human chimeric antibody and a humanized antibody can be obtained by introducing the human chimeric antibody expression vector and the humanized antibody expression vector mentioned in the above 3(3) and (6) into an appropriate host cell. The methods for introducing the expression vector into host cell are an electroporation method (*Cytotechnology*, 3, 133-140 (1990)), and the like. With regard to the host cell into which human chimeric antibody expression vector and humanized antibody expression vector are introduced, any cell may be used so long as it is a host cell which can express the human chimeric antibody and the humanized antibody. Examples thereof include mouse SP2/0-Ag14 cell (ATCC CRL1581), mouse P3X63-Ag8.653 cell (ATCC CRL1580), dihydrofolate reductase gene (hereinafter, referred to as dhfr)-deficient CHO cell (*Proceedings of the National Academy of Sciences of the United States of America*, 77, 4216-4220 (1980)), rat YB2/3HL.P2.G11.16Ag.20 cell (ATCC CRL1662; hereinafter, referred to as YB2/0 cell) and the like.

After introducing the expression vector, a transformant in which human chimeric antibody and humanized antibody are stably expressed can be selected by culturing in a medium for animal cell culture containing an agent such as G418 sulfate (hereinafter, referred to as G418) according to a process disclosed in Japanese Published Unexamined Patent Application NO. 257891/90. With regard to a medium for culturing animal cell, RPMI 1640 medium (manufactured by Nissui Seiyaku), GIT medium (manufactured by Nippon Seiyaku), EX-CELL 302 medium (manufactured by JRH), IMDM (manufactured by Gibco BRL), Hybridoma-SFM (manufactured by Gibco BRL), a medium obtained by adding various additives such as FBS thereto, and the like may be used. When the resulting transformant cell is cultured in a medium, a human chimeric antibody and a humanized antibody can be expressed and accumulated in the culture supernatant. The amount of the human chimeric antibody and the humanized antibody expressed in the culture supernatant and antigen binding activity can be measured by ELISA. Further, in the transformant cell, the amount of the human chimeric antibody and the humanized antibody expressed can be increased by utilizing a dhfr system or the like according to a method disclosed in Japanese Published Unexamined Patent Application NO. 257891/90.

A human chimeric antibody and a humanized antibody can be purified from the culture supernatant of the transformant cell using a protein A column (*Antibodies: A Laboratory Manual*, Cold Spring Harbor Laboratory, Chapter 8 (1988); *Monoclonal Antibodies: Principles and Practice*, Academic Press Limited (1996)). Besides that, purifying methods which are generally used for purification of proteins can be used. For example, gel filtration, ion-exchange chromatography and ultrafiltration may be conducted in combination so as to purify. Molecular weight of H chain and L chain of the purified human chimeric antibody and humanized antibody or of the whole antibody molecular can be determined by polyacrylamide gel electrophoresis (hereinafter, referred to as PAGE; *Nature*, 227, 680-685 (1970), a western blotting method (*Antibodies: A Laboratory Manual*, Cold Spring Harbor Laboratory, Chapter 12 (1988); *Monoclonal Antibodies: Principles and Practice*, Academic Press Limited (1996)), and the like.

(9) Evaluation of Binding Activity of Human Chimeric Antibody and Humanized Antibody to Antigen Binding activity of the human chimeric antibody and the humanized antibody to antigen can be carried out using ELISA mentioned above.

4. Preparation of Antibody Fragment

An antibody fragment can be prepared from the antibody mentioned in the above 1 and 3 by genetic engineering techniques or protein chemical techniques.

Examples of the genetic engineering techniques include a method where gene encoding a desired antibody fragment is constructed and expression using a suitable host such as animal cells, plant cells, insect cells, *Escherichia coli*, or the like and purification are conducted.

Examples of the protein chemical techniques include a method of site-specific cleavage using a protease such as pepsin and papain, and the like or purification.

A process for producing Fab, F(ab')$_2$, Fab', scFv, diabody, dsFv or peptide comprising CDR as a antibody fragment will be specifically illustrated below.

(1) Preparation of Fab

Fab can be prepared by treating IgG with protease, papain in the protein chemical techniques. After the treatment with papain, it is possible to recover as uniform Fab by passing it through a protein A column to separate from IgG molecule and Fc fragment provided that the original antibody is an IgG subclass having a binding property to protein A (*Monoclonal Antibodies: Principles and Practice*, third edition (1995)). In the case of an antibody of an IgG subclass having no binding property to protein A, Fab can be recovered by ion-exchange chromatography at a fraction eluted by a low salt concentration (*Monoclonal Antibodies: Principles and Practice*, third edition (1995)).

Fab can also be prepared by genetic engineering techniques using *E. coli* in many cases or using insect cells, animal cells, and the like. For example, DNA encoding V region of the antibody mentioned in the above 3(2), 3(4) and 3(5) is cloned into a vector for expression of Fab whereupon Fab expression vector can be prepared. With regard to vector for expression of Fab, any vector may be used so long as DNA for Fab can be inserted and expressed. Examples include pIT 106 (*Science*, 240, 1041-1043 (1988)) and the like. The Fab expression vector is introduced into appropriate *E. coli* whereby Fab can be formed and accumulated in an inclusion body or a periplasm. From the inclusion body, active Fab can be obtained by a refolding method generally used for proteins and, when expressed in periplasm, active Fab leaks out in a culture supernatant. After the refolding or from the culture supernatant, uniform Fab can be purified using a column to which antigen is bound (*Antibody Engineering, A Practical Guide*, W H. Freeman and Company (1992)).

(2) Preparation of F(ab')$_2$

F(ab')$_2$ can be prepared by treating of IgG with protease, pepsin in the protein chemical techniques. After the treatment with pepsin, it can be recovered as uniform F(ab')$_2$ by the same purifying operation as in the case of Fab (*Monoclonal Antibodies: Principles and Practice*, third edition, Academic Press (1995)). It can also be prepared by a method where Fab' mentioned in the following 4(3) is treated with a maleimide such as o-PDM or bismaleimide hexane to form a thioether bond or by a method where it is treated with DTNB [5,5'-dithiobis(2-nitrobenzoic acid)] to form an S—S bond (*Antibody Engineering, A Practical Approach*, IRL Press (1996)).

(3) Preparation of Fab'

Fab' can be prepared by treating F(ab')$_2$ mentioned in the above 4(2) with a reducing agent such as dithiothreitol. Fab' can be prepared in the genetic engineering techniques using *E. coli* in many cases or using insect cells, animal cells, and the like. For example, DNA encoding V region of the antibody mentioned in the above 3(2), 3(4) and 3(5) is cloned to a vector for expression of Fab' whereupon Fab' expression vector can be prepared. With regard to a vector for expression of Fab', any vector may be used so long as DNA for Fab' can be integrated and expressed. Examples thereof include pAK 19 (*Bio/Technology*, 10, 163-167 (1992)) and the like. The Fab' expression vector is introduced into appropriate *E. coli* to form and accumulate Fab' in an inclusion body or periplasm. From the inclusion body, active Fab' can be obtained by a refolding method which is generally used in proteins and, when the Fab' is expressed in periplasm, it can be recovered extracellulary by disrupting the cell with a treatment such as partial digestion by lysozyme, osmotic shock and sonication and the like. After the refolding or from the disrupted cell solution, uniform Fab' can be purified using a protein G column or the like (*Antibody Engineering, A Practical Approach*, IRL Press (1996)).

(4) Preparation of scFv scFv can be prepared using phage or *E. coli* or using insect cells or animal cells by genetic engineering techniques. For example, DNA encoding V region of the antibody mentioned in the above 3(2), 3(4) and 3(5) is cloned into a vector for expression of scFv whereupon a scFv expression vector can be prepared. With regard to the vector for expression of scFv, any vector may be used so long as the DNA of scFv can be inserted and expressed. Examples thereof include pCANTAB5E (manufactured by Pharmacia), pHFA (*Human Antibodies & Hybridomas*, 5, 48-56 (1994)), and the like. When the scFv expression vector is introduced into appropriate *E. coli* and a helper phage is infected, a phage which expresses scFv on the phage surface in a fused form with the surface protein of the phage can be obtained. Also, scFv can be formed and accumulated in periplasm or an inclusion body of *E. coli* into which scFv expression vector is introduced. From the inclusion body, active scFv can be obtained by a refolding method generally used for proteins and, when scFv is expressed in periplasm, it can be recovered extracellulary by disrupting the cell with a treatment such as partial digestion by lysozyme, osmotic shock and sonication and the like. After the refolding or from the disrupted cell solution, uniform scFv can be purified using cation-exchange chromatography or the like (*Antibody Engineering, A Practical Approach*, IRL Press (1996)).

(5) Preparation of Diabody

Diabody can be prepared using *E. coli* in many cases or using insect cells, animal cells, and the like in the genetic engineering techniques. For example, DNAs in which VH and VL of the antibody mentioned in the above 3(2), 3(4) and 3(5) are linked by a linker coding 8 amino acid residues or less is prepared and cloned into a vector for expression of diabody whereupon a diabody expression vector can be prepared. With regard to a vector for expression of diabody, any vector may be used so long as the DNA of diabody can be integrated and expressed. Examples thereof include pCANTAB5E (manufactured by Pharmacia), pHFA (Human Antibodies Hybridomas, 5, 48 (1994)) and the like. Diabody can be formed and accumulated in periplasm or inclusion body of *E. coli* into which a diabody expression vector is introduced. From the inclusion body, active diabody can be obtained by a refolding method generally used for proteins and, when the diabody is expressed in periplasm, it can be recovered extracellulary by disrupting the cell with treatment such as partial digestion by lysozyme, osmotic shock and sonication and the like. After the refolding or from the disrupted cell solution, uniform diabody can be purified using cation-exchange chromatography or the like (Antibody Engineering, A Practical Approach, IRL Press (1996)).

(6) Preparation of dsFv dsFv can be prepared using *E. coli* in many cases or using insect cells, animal cells, and the like in the genetic engineering techniques. Firstly, mutation is introduced into an appropriate position of DNA encoding VH and VL of the antibody mentioned in the above 3(2), 3(4) and 3(5) to prepare DNAs in which an encoded amino acid residue is replaced with cysteine. Each DNA prepared as such is cloned to a vector for expression of dsFv whereby an expression vector of VH and VL can be prepared. With regard to a vector for expression of dsFv, any vector may be used so long as the DNA for dsFv can be integrated and expressed. Examples thereof include pULI 9 (*Protein Engineering*, 7, 697-704 (1994)) and the like. The expression vector of VH and VL is introduced into appropriate *E. coli* and dsFv is formed and accumulated in an inclusion body or periplasm. VH and VL are obtained from the inclusion body or periplasm, mixed and subjected to a refolding method generally used for proteins to thereby obtain active dsFv. After the refolding, it can be further purified by ion-exchange chromatography, gel filtration, and the like. (*Protein Engineering*, 7, 697-704 (1994)).

(7) Preparation of Peptide Comprising CDR

Peptide comprising CDR can be prepared by a chemical synthesis method such as an Fmoc method or a tBoc method. Further, DNA encoding a peptide comprising CDR is prepared and the resulting DNA is cloned to an appropriate vector for expression whereby a peptide comprising CDR expression vector can be prepared. With regard to a vector for expression, any vector may be used so long as the DNA which encodes peptide comprising CDR can be inserted and expressed. Examples thereof include pLEX (manufactured by Invitrogen), pAX4a+ (manufactured by Invitrogen) and the like. The expression vector is introduced into appropriate *E. coli* and formed and accumulated in an inclusion body or periplasm. From the inclusion body or periplasm, the peptide comprising CDR is obtained and it can be purified by ion-exchange chromatography, gel filtration and the like (*Protein Engineering*, 7, 697-704 (1994)).

(8) Evaluation of Binding Activity of Antibody Fragment to Antigen

Evaluation of binding activity of the purified antibody fragment to an antigen can be carried out using ELISA mentioned in the above 1(7).

5. Therapeutic Agent of the Present Invention

A therapeutic agent for endometriosis of the present invention can be any medicament so long as it comprises IL-5 antagonist as an active ingredient, but it is generally preferred to provide it in the form of a pharmaceutical formulation produced by mixing it with one or more pharmaceutically acceptable carriers in accordance with any method well known in the technical field of pharmaceutics. Preferably, an aseptic solution where it is dissolved in an aqueous carrier such as water, or an aqueous solution of salt, glycine, glucose or human albumin is used. It is also possible to add a pharmaceutically acceptable additive such as buffer or isotonizing agent for making the preparation solution more similar to the physiological conditions and examples thereof include sodium acetate, sodium chloride, sodium lactate, potassium chloride, sodium citrate and the like. It may also be preserved by freeze-drying and, in actual use, it may be used by dissolving in an appropriate solvent.

With regard to the administration route of the therapeutic agent of the present invention, it is preferred to use the most effective route for the treatment. Examples thereof include oral administration and parenteral administration such as intraoral, tracheobronchial, intrarectal, subcutaneous, intramuscular and intravenous, and, among them, intravenous administration is preferred.

Examples of the preparation suitable for the oral administration include emulsion, syrup, capsule, tablet, diluted powder, granule and the like. Liquid preparation such as emulsion and syrup can be prepared using water, saccharides such as sucrose, sorbitol and fructose, glycols such as polyethylene glycol and propylene glycol, oils such as sesame oil, olive oil and soybean oil, antiseptics such as p-hydroxybenzoate, flavors such as strawberry flavor and peppermint flavor and the like as additives. Capsule, tablet, diluted powder, granule, and the like can be prepared using excipients such as lactose, glucose, sucrose and mannitol, disintegrating agents such as starch and sodium alginate, lubricants such as magnesium stearate and talc, binders such as polyvinyl alcohol, hydroxypropyl cellulose and gelatin, surfactants such as fatty acid ester, plasticizers such as glycerol, as additives.

Examples of the preparation suitable for parenteral administration include injection, suppository, air spray and the like. For example, injection is prepared using a carrier comprising salt solution, glucose solution or a mixture of both, or the like. Suppository is prepared using a carrier such as cacao butter, hydrogenated fat or carboxylic acid. Air spray is prepared using the antagonist as such or using, for example, a carrier which does not stimulate the mouth and the airway mucous membrane of a person to be administered, and which disperses the antagonist into fine particles and makes the absorption easy. Specific examples of the carrier include lactose, glycerol and the like. Depending upon the property of the antagonist and the carrier used, it is possible to prepare aerosol, dry powder, and the like. In addition, even in the parenteral preparation, components exemplified as additives in the oral preparation may be added.

Dose or the number of administration of the therapeutic agent of the present invention varies depending upon desired therapeutic effect, administering method, period for the treatment, age, body weight, and the like and, usually, it is 10 µg/kg to 10 mg/kg per day for an adult.

The present invention is described in the following Examples.

Example 1

Suppressive Activity of Anti-IL-5 Receptor Antibody and Anti-IL-5 Antibody to Autotransplantation Model of Rat Endometriosis With regard to a suppressive activity of anti-IL-5 receptor antibody and anti-IL-5 antibody using autotransplantation model of rat endometriosis, the following experiments were carried out.

As to a method therefor, a known method [*Fertility and Sterility*, 44, 684-694 (1985)] was modified and used.

Female rats of SD strain of not younger than eight weeks old (Nippon Charles River) which was believed to be in sex maturation were purchased and their sexual cycle was measured every day using a vagina impedance checker for rats (MK-10B manufactured by Muromachi Kikaisha). Among the rats where a sexual cycles of 4 to 5 days were observed for twice or more, those in a stage of proestrus were selected and subjected to autotransplantation of endometrial tissues as mentioned below.

After the test drug was intravenously administered to rats, abdomens of rats subjected to general anesthesia by intraperitoneal administration of pentobarbital (Somnopentyl® manufactured by Takeda Schering Plough Animal Health) were shaved and opened up in about 6 cm along the central line. Among the uteruses bicornate, an upper area of about 1 cm from the root of the right uterus and a lower area of about 2 cm from ovary were ligated and the uterus between them was excised. The excised uterus (tubular) was opened longitudinally while washing with a Dulbecco's modified Eagle medium (manufactured by Invitrogen) containing penicillin-streptomycin (manufactured by Invitrogen) to make into a sheet. From this sheet, an endometrial piece of about 2 mm square was prepared. The endometrial pieces prepared as such were subjected to autotransplantation to right and left peritonea using a suture needle equipped with an sterilized thread (a slightly curved needle for surgical operations No. 12-black Nylon No. 6-0, manufactured by Natsume Seisakusho). At that time, autotransplantation was conducted so that the endometrial surface comes in contact with the peritoneum. As a control, fat tissue in the same size as the endometrial piece was excised from the same rat and similarly autotransplanted to the peritoneum. Finally, the transplanted site and the site wherefrom the uterus was excised were washed with a physiological saline solution containing micronomicin (Sagamicin® injection, manufactured by Kyowa Hakko Kogyo) and the peritoneum and the skin were sutured immediately with care by a suture needle equipped with an sterilized thread.

After one week from autotransplantation, the rat was sacrificed by exsauguination under anesthetizing with ether, the abdomen was opened and the evaluation of endometrial lesion (measurement of the size of the transplanted piece) was conducted by naked eye. With regard to the size of the transplanted piece, diameters in longitudinal and transverse directions were measured using die micrometer calipers (minimum scale: 0.5 mm). The test was conducted where one group is comprised of five rats. If necessary, pathological specimen of the transplanted site was prepared according to a common method and a histopathological analysis was carried out.

As a test drug, 1 mg/kg of anti-mouse IL-5 receptor antibody and anti-mouse IL-5 antibody (*International Immunology*, 322, 135-9 (1991)) were used while 1 mg/kg of rat IgG antibody (manufactured by ICN) was used as a control antibody. All of the antibodies were used after diluting with a sterilized phosphate buffer (manufactured by ICN).

The result for the size of the transplanted piece is shown in Table 1. With regard to the size of the transplanted piece, value calculated by multiplication of longitudinal diameter by transverse diameter was used and the average size of the right and left transplanted pieces was shown.

As shown in Table 1, the size of the transplanted piece which increased after one week from the transplantation was decreased by administration of the anti-IL-5 antibody and the anti-IL-5 receptor antibody (suppressive rate: 14% for the anti-IL-5 antibody and 15% for the anti-IL-5-receptor antibody).

TABLE 1

| Administered group | Dose (mg/kg) | Administration route | Number of doses | Size of transplanted piece (mm$^2$) |
|---|---|---|---|---|
| Control antibody | 1 | Intravenously | Once immediately before transplantation | 16.8 ± 3.3 |
| Anti-IL-5 receptor antibody | 1 | Intravenously | Once immediately before transplantation | 14.3 ± 2.3 |
| Anti-IL-5 antibody | 1 | Intravenously | Once immediately before transplantation | 14.4 ± 1.1 |

Example 2

Suppressive Activity of Anti-IL-5R Antibody for the Adhesion in Autotransplantation Model of Rat Endometriosis The following experiment was carried out using autotransplantation model of rat endometriosis in order to confirm that the anti-IL-5 receptor antibody suppresses the adhesion of the endometrium. The experiment was conducted according to the method mentioned in Example 1.

Female rats of SD strain of not younger than eight weeks old (manufactured by Nippon Charles River) which was believed to be in sex maturation were purchased and their sexual cycle was measured every day using a vagina impedance checker for rats (MK-10B manufactured by Muromachi Kikaisha). Among the rats where a sexual cycles of 4 to 5 days was observed for twice or more, those in a stage of proestrus were selected and subjected to autotransplantation of endometrial tissues as mentioned below.

After the test drug was intravenously administered to rats, abdomens of rats subjected to general anesthesia by intraperitoneal administration of pentobarbital (Somnopentyl® manufactured by Takeda Schering Plough Animal Health) were shaved and open up in about 6 cm along the central line. Among the uteruses bicornate, an upper area of about 1 cm from the root of the right uterus and a lower area of about 2 cm from ovary were ligated and the uterus between them was excised. The excised uterus (tubular) was opened longitudinally while washing with a Dulbecco's modified Eagle medium (manufactured by Invitrogen) containing penicillin-streptomycin (manufactured by Invitrogen) to make into a sheet. From this sheet, an endometrial piece of about 2 mm square was prepared. The endometrial pieces prepared as such were subjected to autotransplantation to right and left peritonea using a suture needle equipped with an sterilized thread (slightly curved needle for surgical operations No. 12-black Nylon No. 6-0, manufactured by Natsume Seisakusho). At that time, autotransplantation was conducted so that the endometrial surface come into contact with the peritoneum. As a control, fat tissue in the same size as the endometrial piece was excised from the same rat and similarly autotransplanted to the peritoneum. Finally, the transplanted site and the site wherefrom the uterus was excised were washed with a physiological saline solution containing micronomicin (Sagamicin® injection, manufactured by Kyowa Hakko Kogyo) and the peritoneum and the skin were sutured immediately with care by a suture needle equipped with an sterilized thread.

After one week from autotransplantation, the rat was sacrificed by exsauguination under anesthetizing with ether, the abdomen was opened and the evaluation of endometrial lesion (adhesion score) was conducted by naked eye. Adhesion was scored according to the following criteria.

the case where no adhesion was noted; score 0 the case where, although adhesion was noted, it was slight; score 1 the case where, although strong adhesion was noted, it was exfoliative; score 2 the case where strong adhesion was noted and it was not exfoliative; score 3

The test was conducted where one group is comprised of five rats. If necessary, pathological specimen of the transplanted site was prepared according to a common method and a histopathological analysis was carried out.

As a test drug, an anti-mouse IL-5 receptor antibody (*International Immunology*, 3(2, 135-9 (1991)) was used. A rat IgG antibody (manufactured by ICN) was used as a control antibody. All of antibodies were used after diluting with a sterilized phosphate buffer (manufactured by ICN).

Result of adhesion scores in the lesion site is shown in Table 2. With regard to the adhesion scores, they are expressed in points and the average adhesion score of right and left transplanted pieces was shown.

TABLE 2

| Administered group | Dose (mg/kg) | Administration route | Number of doses | Adhesion score |
|---|---|---|---|---|
| Control antibody | 1 | Intravenously | Once immediately before transplantation | 1.4 ± 0.5 |
| Anti-IL-5 receptor antibody | 1 | Intravenously | Once immediately before transplantation | 1.0 ± 0.4 |

As shown in Table 2, in autotransplantation model of rat endometriosis, adhesion observed in the lesion site of patients suffering from endometriosis which was observed clinically was clearly noted. Against the adhesion score as such, there was a tendency of suppression in the group to which an anti-IL-5 receptor antibody was administered (suppressive rate: 29%). Incidentally, when fat tissue was transplanted as a control, adhesion was hardly observed.

Example 3

Suppressive Activity of Anti-Mouse IL-5 Receptor Antibody to Formation Of Endometrial Lesion in Model of Mouse Endometriosis The following experiment was carried out in order to test the efficacy of an anti-IL-5 receptor antibody to endometriosis.

As a method therefor, a known method [*Human Reproduction*, 14, 2944-2950 (1999)] was modified and used.

Male Balb/c strain mice of not younger than eight weeks old (Nippon Charles River) which was believed to be in sex maturation were purchased and used for the experiment. After an adapting period for one week from the purchase, all mice were subjected to an excision operation of right and left ovaries for making the sex hormone environment uniform and then estrogen was exogenously administered. Thus, the skin of the back of mice subjected to a general anesthesia by an intraperitoneal administration of 50 mg of pentobarbital (Somnopentyl® manufactured by Takeda Schering Plough Animal Health) was incised about 1 cm along the central line and a cut (about 3 mm) was made in peritoneum where right and left ovaries were present. After the ovaries on both sides were excised from the cut, the skin of the back was quickly sutured and returned to a breeding cage. After that, 100 μg/kg of estrogen (Progynone Depot 10 mg, manufactured by Nippon Schering, estradiol valerate injection) was injected into the muscle of left hind paw. As a result of the treatment as such, it was confirmed that uterus swells to such a weight that nearly the same as a mouse uterus during the proestrus which is a high-estrogen period in a sexual cycle noted every four days in mice.

Then, after one week from excision of ovaries, all mice were divided into donor mice and recipient mice in a constituting ratio of 1:2 and endometrial piece prepared by excision of uterus of the donor mouse was inoculated into the abdomen of the recipient mouse. Thus, surrounding fat tissues and uterine necks were removed from the right and left uteruses excised from the donor mouse which was sacrificed by exsauguination and the uterus body in which endometrium was contained was finely cut by small scissors for surgical operation to prepare pieces. The endometrial pieces were suspended in a sterilized HBSS (a Hank's balanced salt solution, manufactured by Sigma) containing an antibiotics and those for all donor mice were pooled. The suspension of the endometrial pieces (0.8 mL; corresponding to about 50 mg as the endometrial pieces) was inoculated by intraperitoneally administering to a recipient mouse which was subjected to general anesthesia with 40 mg/kg of pentobarbital using a syringe equipped with a 19G injection needle (manufactured by Thermo). Filling of the suspension of the endometrial pieces into a syringe and administration thereof were carried out by means of well stirring of the suspension so that the liquid did not become ununiformly. After that, 100 μg/kg of estrogen and sesame oil which is a solvent for estrogen were intramuscularly administered once a week to both of a positive control group and a drug-evaluating group and to a negative control group, respectively.

After three weeks from inoculation of the endometrial pieces, the mice were sacrificed by exsauguination, the abdomen was opened up and evaluation of endometrial lesion by naked eye (measurement of size of the formed cyst) was carried out. With regard to the size of the lesion, diameters in longitudinal and transverse directions were measured using die micrometer calipers (minimum scale: 0.5 mm) and evaluation was conducted by an area calculated by multiplication of the longitudinal diameter by the transverse diameter. When a plurality of lesion was formed, their total sum was evaluated as a total area and the test was conducted where one group is comprised of ten mice. If necessary, pathological specimen of the transplanted site was prepared according to a common method and a histopathological analysis was carried out.

As a test drug, an anti-mouse IL-5 receptor antibody (*International Immunology*, 3(2):135-9 (1991); 10 mg/kg, administered once a week) was used. In a positive control group, a rat IgG antibody (manufactured by ICN; 10 mg/kg, administered once a week) was used as a control antibody. All antibodies were used after diluting with a sterilized physiological saline solution (manufactured by Otsuka Pharmaceutical).

Result for the lesion size is shown in FIG. 1.

After three weeks from inoculation of the endometrial pieces, the onset rate of lesion was 100% in the positive control group while, in a negative control group, the onset was noted only in one mouse. All of the formed lesions were cysts lined with endometrial epithelium whereby it was confirmed to be endometriosis lesion by means of histopathology. Thus, the present experimental models are believed to be useful models which reflected endometriosis growing in an estrogen-dependent manner.

In the present models, an anti-mouse IL-5 receptor antibody showed a significant suppressive activity as compared with a positive control group as shown in FIG. 1. Incidentally, when pieces of mucosae of small intestine in the same weight were inoculated instead of endometrial pieces, lesion was not formed at all even by administration of estrogen.

Example 4

Suppressive Activity of Anti-Mouse IL-5 Antibody to Formation of Endometrial Lesion in Model of Mouse Endometriosis Efficacy of an anti-IL-5 antibody to endometriosis was tested according to the method mentioned in Example 3.

The experimental method conducted was the same as that mentioned in Example 3 except that an anti-mouse IL-5 antibody (*International Immunology*, 3(2), 135-9 (1991); 1 and 10 mg/kg, administered once a week) was used as a test drug instead of an anti-mouse IL-5 receptor antibody.

Result of the lesion size is shown in FIG. 2.

An anti-mouse IL-5 antibody showed a significant suppressive activity in a group where 10 mg/kg was administered as compared with a positive control group.

INDUSTRIAL APPLICABILITY

The present invention provides a therapeutic agent for endometriosis comprising an interleukin-5 antagonist as an active ingredient.

Free Text of Sequence Listing:

SEQ ID NO:9—Explanation for synthetic sequence: Antibody heavy chain variable region amino acid sequence
SEQ ID NO:10—Explanation for synthetic sequence: Antibody light chain variable region amino acid sequence
SEQ ID NO:11—Explanation for synthetic sequence: Antibody heavy chain variable region amino acid sequence
SEQ ID NO:12—Explanation for synthetic sequence: Antibody heavy chain variable region amino acid sequence
SEQ ID NO:13—Explanation for synthetic sequence: Antibody heavy chain variable region amino acid sequence
SEQ ID NO:14—Explanation for synthetic sequence: Antibody light chain variable region amino acid sequence
SEQ ID NO:15—Explanation for synthetic sequence: Antibody light chain variable region amino acid sequence
SEQ ID NO:16—Explanation for synthetic sequence: Antibody light chain variable region amino acid sequence
SEQ ID NO:17—Explanation for synthetic sequence: Antibody light chain variable region amino acid sequence

The invention claimed is:

1. A method for treating endometriosis which comprises administering an interleukin-5 antagonist to a patient in need thereof.

2. The method according to claim 1, wherein the interleukin-5 antagonist is an antibody which inhibits the binding of interleukin-5 to an interleukin-5 receptor or an antibody fragment thereof.

3. The method according to claim 2, wherein the antibody which inhibits the binding of interleukin-5 to an interleukin-5 receptor is an antibody which binds to interleukin-5.

4. The method according to claim 3, wherein interleukin-5 is human interleukin-5.

5. The method according to claim 2, wherein the antibody which inhibits the binding of interleukin-5 to an interleukin-5 receptor is an antibody which binds to an interleukin-5 receptor.

6. The method according to claim 5, wherein the interleukin-5 receptor is interleukin-5 receptor α chain.

7. The method according to claim 5, wherein the interleukin-5 receptor is a human interleukin-5 receptor.

8. The method according to claim 2, wherein the antibody is a monoclonal antibody.

9. The method according to claim 8, wherein the monoclonal antibody is a gene recombinant antibody.

10. The method according to claim 9, wherein the gene recombinant antibody is a gene recombinant antibody selected from the group consisting of a human chimeric antibody, a humanized antibody and a human antibody.

11. The method according to claim 2, wherein the antibody fragment is an antibody fragment selected from Fab, Fab', F(ab')$_2$, single chain antibody (scFv), dimerized variable region (diabody), disulfide stabilized variable region (dsFv) and a peptide comprising CDR.

* * * * *